(12) United States Patent
Germain et al.

(10) Patent No.: US 9,603,656 B1
(45) Date of Patent: Mar. 28, 2017

(54) ARTHROSCOPIC DEVICES AND METHODS

(71) Applicant: RELIGN Corporation, Cupertino, CA (US)

(72) Inventors: Aaron Germain, San Jose, CA (US); Kyle Klein, San Jose, CA (US); Michael D. Walker, San Francisco, CA (US); Ben Poser, Santa Cruz, CA (US)

(73) Assignee: RELIGN Corporation, Cupertino, CA (US)

( * ) Notice: Subject to any disclaimer, the term of this patent is extended or adjusted under 35 U.S.C. 154(b) by 0 days.

(21) Appl. No.: 14/977,256

(22) Filed: Dec. 21, 2015

Related U.S. Application Data

(60) Provisional application No. 62/250,315, filed on Nov. 3, 2015, provisional application No. 62/245,796, filed on Oct. 23, 2015.

(51) Int. Cl.
*A61B 18/14* (2006.01)
*A61B 17/32* (2006.01)
(Continued)

(52) U.S. Cl.
CPC ...... *A61B 18/149* (2013.01); *A61B 17/32002* (2013.01); *A61B 18/14* (2013.01);
(Continued)

(58) Field of Classification Search
CPC ............ A61B 18/149; A61B 17/32002; A61B 2018/00577; A61B 2218/007;
(Continued)

(56) References Cited

U.S. PATENT DOCUMENTS 2,513,564 A 7/1950 Ingwersen
2,514,545 A 7/1950 Ingwersen
(Continued)

FOREIGN PATENT DOCUMENTS

DE 102005059864 A1 6/2007
EP 1034747 A1 9/2000
(Continued)

OTHER PUBLICATIONS

U.S. Appl. No. 14/960,084, filed Dec. 4, 2015, Germain et al.
(Continued)

*Primary Examiner* — Jaymi Della
*Assistant Examiner* — Eunhwa Kim
(74) *Attorney, Agent, or Firm* — Wilson Sonsini Goodrich & Rosati

(57) ABSTRACT

A medical device includes an elongated sleeve having a longitudinal axis, a proximal end and a distal end. A cutting member having a plurality of sharp edges is formed from a wear-resistant ceramic material is carried at the distal end of the elongated sleeve. A motor drive is coupled to the proximal end of the elongated sleeve to rotate the sleeve at cutting member at high RPMs to cut bone and other hard tissue. An electrode is carried in a distal portion of ceramic cutting member for RF ablation of tissue when the sleeve and cutting member are is a stationary position. In methods of use, (i) the ceramic member can be engaged against bone and then rotated at high speed to cut bone tissue, and (ii) the ceramic member can be held in a stationary (non-rotating) position to engage tissue and RF energy can be delivered to the electrode to create a plasma that ablates tissue.

18 Claims, 19 Drawing Sheets

(51) Int. Cl.
*A61B 18/00* (2006.01)
*A61B 17/00* (2006.01)
(52) U.S. Cl.
CPC ......... *A61B 18/148* (2013.01); *A61B 18/1482* (2013.01); *A61B 18/1485* (2013.01); *A61B 2017/00039* (2013.01); *A61B 2018/00577* (2013.01); *A61B 2018/00601* (2013.01); *A61B 2218/007* (2013.01)
(58) Field of Classification Search
CPC ........... A61B 2017/00039; A61B 2018/00601; A61B 18/14; A61B 18/148; A61B 18/1482; A61B 18/1485
See application file for complete search history.

(56) References Cited

U.S. PATENT DOCUMENTS

| | | | |
|---|---|---|---|
| 2,625,625 A | 1/1953 | Ingwersen | |
| 2,689,895 A | 9/1954 | Ingwersen | |
| 3,611,023 A | 10/1971 | Souza, Jr. et al. | |
| 3,838,242 A | 9/1974 | Goucher | |
| 3,848,211 A | 11/1974 | Russell | |
| 3,868,614 A | 2/1975 | Riendeau | |
| 3,903,891 A | 9/1975 | Brayshaw | |
| 4,060,088 A | 11/1977 | Morrison, Jr. et al. | |
| 4,272,687 A | 6/1981 | Borkan | |
| 4,781,175 A | 11/1988 | McGreevy et al. | |
| 4,977,346 A | 12/1990 | Gibson et al. | |
| 5,012,495 A | 4/1991 | Munroe et al. | |
| 5,122,138 A | 6/1992 | Manwaring | |
| 5,207,675 A | 5/1993 | Canady | |
| 5,256,138 A | 10/1993 | Burek et al. | |
| 5,281,217 A | 1/1994 | Edwards et al. | |
| 5,449,356 A | 9/1995 | Walbrink et al. | |
| 5,490,854 A * | 2/1996 | Fisher ................... | A61B 17/15 606/79 |
| 5,641,251 A | 6/1997 | Leins et al. | |
| 5,669,907 A | 9/1997 | Platt, Jr. et al. | |
| 5,683,366 A | 11/1997 | Eggers et al. | |
| 5,720,745 A | 2/1998 | Farin et al. | |
| 5,759,185 A | 6/1998 | Grinberg | |
| 5,776,092 A | 7/1998 | Farin et al. | |
| 5,849,010 A | 12/1998 | Wurzer et al. | |
| 5,873,855 A | 2/1999 | Eggers et al. | |
| 5,888,198 A | 3/1999 | Eggers et al. | |
| 5,891,095 A | 4/1999 | Eggers et al. | |
| 5,904,681 A * | 5/1999 | West, Jr. ............. | A61B 18/1485 604/22 |
| 5,913,867 A | 6/1999 | Dion | |
| 5,964,752 A | 10/1999 | Stone | |
| 5,989,248 A | 11/1999 | Tu et al. | |
| 6,013,075 A | 1/2000 | Avramenko et al. | |
| 6,013,076 A | 1/2000 | Goble et al. | |
| 6,024,733 A | 2/2000 | Eggers et al. | |
| 6,032,674 A | 3/2000 | Eggers et al. | |
| 6,039,736 A | 3/2000 | Platt, Jr. | |
| 6,056,747 A | 5/2000 | Saadat et al. | |
| 6,066,134 A | 5/2000 | Eggers et al. | |
| 6,099,523 A | 8/2000 | Kim et al. | |
| 6,142,992 A | 11/2000 | Cheng et al. | |
| 6,149,620 A | 11/2000 | Baker et al. | |
| 6,159,208 A | 12/2000 | Hovda et al. | |
| 6,225,883 B1 | 5/2001 | Wellner et al. | |
| 6,235,020 B1 | 5/2001 | Cheng et al. | |
| 6,238,391 B1 | 5/2001 | Olsen et al. | |
| 6,296,636 B1 | 10/2001 | Cheng et al. | |
| 6,332,886 B1 | 12/2001 | Green et al. | |
| 6,348,051 B1 | 2/2002 | Farin et al. | |
| 6,394,956 B1 | 5/2002 | Chandrasekaran et al. | |
| 6,413,256 B1 | 7/2002 | Truckai et al. | |
| 6,419,674 B1 | 7/2002 | Bowser et al. | |
| 6,443,948 B1 | 9/2002 | Suslov | |
| 6,475,215 B1 | 11/2002 | Tanrisever | |
| 6,538,549 B1 | 3/2003 | Renne et al. | |
| 6,579,289 B2 | 6/2003 | Schnitzler | |
| 6,632,220 B1 | 10/2003 | Eggers et al. | |
| 6,656,195 B2 * | 12/2003 | Peters ............... | A61B 17/32002 606/159 |
| 6,669,694 B2 | 12/2003 | Shadduck | |
| 6,720,856 B1 | 4/2004 | Pellon et al. | |
| 6,780,178 B2 | 8/2004 | Palanker et al. | |
| 6,783,533 B2 | 8/2004 | Green et al. | |
| 6,821,275 B2 | 11/2004 | Truckai et al. | |
| 6,837,884 B2 | 1/2005 | Woloszko | |
| 6,890,332 B2 | 5/2005 | Truckai et al. | |
| 6,902,564 B2 | 6/2005 | Morgan et al. | |
| 7,087,054 B2 | 8/2006 | Truckai et al. | |
| 7,220,261 B2 | 5/2007 | Truckai et al. | |
| 7,309,849 B2 | 12/2007 | Truckai et al. | |
| 7,549,989 B2 | 6/2009 | Morgan et al. | |
| 7,713,269 B2 | 5/2010 | Auge, II et al. | |
| 7,717,710 B2 | 5/2010 | Danger et al. | |
| 7,744,595 B2 | 6/2010 | Truckai et al. | |
| 7,771,422 B2 | 8/2010 | Auge, II et al. | |
| 7,819,861 B2 | 10/2010 | Auge, II et al. | |
| 7,819,864 B2 | 10/2010 | Morgan et al. | |
| 7,955,331 B2 | 6/2011 | Truckai et al. | |
| 8,016,823 B2 | 9/2011 | Shadduck | |
| 8,062,319 B2 | 11/2011 | O'Quinn et al. | |
| 8,075,555 B2 | 12/2011 | Truckai et al. | |
| 8,192,424 B2 | 6/2012 | Woloszko | |
| 8,192,428 B2 | 6/2012 | Truckai et al. | |
| 8,221,404 B2 | 7/2012 | Truckai | |
| 8,323,280 B2 | 12/2012 | Germain et al. | |
| 8,333,763 B2 | 12/2012 | Truckai et al. | |
| 9,179,923 B2 | 11/2015 | Gubellini et al. | |
| 2003/0014051 A1 | 1/2003 | Woloszko | |
| 2003/0083681 A1 * | 5/2003 | Moutafis ............ | A61B 17/1633 606/167 |
| 2003/0125727 A1 | 7/2003 | Truckai et al. | |
| 2003/0163135 A1 | 8/2003 | Hathaway | |
| 2004/0044341 A1 | 3/2004 | Truckai et al. | |
| 2005/0075630 A1 | 4/2005 | Truckai et al. | |
| 2005/0228372 A1 | 10/2005 | Truckai et al. | |
| 2006/0058782 A1 | 3/2006 | Truckai et al. | |
| 2006/0224154 A1 | 10/2006 | Shadduck et al. | |
| 2007/0213704 A1 | 9/2007 | Truckai et al. | |
| 2008/0208249 A1 | 8/2008 | Blain et al. | |
| 2009/0076498 A1 | 3/2009 | Saadat et al. | |
| 2009/0270849 A1 | 10/2009 | Truckai et al. | |
| 2010/0100091 A1 | 4/2010 | Truckai | |
| 2010/0305565 A1 | 12/2010 | Truckai et al. | |
| 2012/0245580 A1 | 9/2012 | Germain et al. | |
| 2012/0330292 A1 | 12/2012 | Shadduck et al. | |
| 2013/0122461 A1 | 5/2013 | Shioiri | |
| 2013/0296849 A1 | 11/2013 | Germain et al. | |
| 2013/0317493 A1 | 11/2013 | Truckai et al. | |

FOREIGN PATENT DOCUMENTS

| | | |
|---|---|---|
| WO | WO 00/53112 A2 | 9/2000 |
| WO | WO 00/62685 A1 | 10/2000 |
| WO | WO 00/53112 A3 | 12/2000 |
| WO | WO 2007/073867 A1 | 7/2007 |

OTHER PUBLICATIONS

European search report dated Nov. 2, 2009 for EP Application No. 01967968.7.

International search report and written opinion dated May 23, 2012 for PCT/US2012/023390.

International search report dated Jan. 14, 2002 for PCT/US2001/025409.

Kim, et al. Optical feedbacksignal for ultra short pulse ablation of tissue. Appl. Surface Sci. 1998; 127-129:857-862.

Pedowitz, et al. Arthroscopic surgical tools: a source of metal particles and possible joint damage. Arthroscopy. Sep. 2013;29(9):1559-65. doi: 10.1016/j.arthro.2013.05.030.Epub Jul. 30, 2013.

(56) References Cited

OTHER PUBLICATIONS

Tucker et al. Histologic characteristics of electrosurgical injuries. J. Am. Assoc. Gyneco. Laproscopy. 1997; 4(2):857-862.
Office action dated May 3, 2016 for U.S. Appl. No. 14/960,084.
International Search Report and Written Opinion dated Nov. 29, 2016 for International Application No. PCT/US2016/058145.
Notice of Allowance dated Jan. 6, 2017 for U.S. Appl. No. 14/960,084.

* cited by examiner

ARTHROSCOPIC DEVICES AND METHODS

CROSS-REFERENCE TO RELATED APPLICATIONS

This application claims the benefit of provisional application 62/250,315, filed on Nov. 3, 2015, and of provisional application 62/245,796, filed on Oct. 23, 2015, the full disclosures of which are incorporated herein by reference.

BACKGROUND OF THE INVENTION

1. Field of the Invention

This invention relates to arthroscopic tissue cutting and removal devices by which anatomical tissues may be cut and removed from a joint or other site. More specifically, this invention relates to instruments configured for cutting and removing bone or other hard tissue and having a ceramic cutting member.

2. Description of the Background Art

In several surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove tissue for such procedures. A typical arthroscopic shaver or burr comprises a metal cutting member carried at the distal end of a metal sleeve that rotates within an open-ended metal shaft. A suction pathway for removal of bone fragments or other tissues is provided through a window proximal to the metal cutting member that communicates with a lumen in the sleeve.

When metal shavers and burrs "wear" during a procedure, which occurs very rapidly when cutting bone, the wear can be accompanied by loss of micro-particles from fracture and particle release which occurs along with dulling due to metal deformation. In such surgical applications, even very small amounts of such foreign particles that are not recovered from a treatment site can lead to detrimental effects on the patient health, with inflammation being typical. In some cases, the foreign particles can result in joint failure due to osteolysis, a term used to define inflammation due to presence of such foreign particles. A recent article describing such foreign particle induced inflammation is Pedowitz, et al. (2013) Arthroscopic surgical tools: "A source of metal particles and possible joint damage", Arthroscopy—The Journal of Arthroscopic and Related Surgery, 29(9), 1559-1565. In addition to causing inflammation, the presence of metal particles in a joint or other treatment site can cause serious problems for future MRIs. Typically, the MRI images will be blurred by agitation of the metal particles caused by the magnetic field used in the imaging, making assessments of the treatment difficult.

Another problem with the currently available metal shavers/burrs relates to manufacturing limitations in combination with the rapid dulling of metal cutting edges. Typically, a metal cutter is manufactured by machining the cutting surfaces and flutes into a burr or abrader surface. The flute shape and geometry can be limited since it is dictated by the machining process, and burr size and shape limitations may direct usage toward more coarse bone removal applications. Further, when operated in a rotational or oscillatory mode, the cutting edges adapted for coarse bone removal may have a kickback effect as the flutes first make contact with bone, which is aggravated by rapid dulling of the machined cutting edges.

Therefore, the need exists for arthroscopic burrs and/or shavers that can operate to cut and remove bone without the release of fractured particles and micro-particles into the treatment site. Further, there is a need for burrs/cutters that do not wear rapidly and that can have cutting edges not limited by metal machining techniques.

As an alternative to such arthroscopic cutters and shavers, another class of tissue removal tools relies on radiofrequency (RF) ablation to remove the soft tissue. Tools such as those described in U.S. Pat. No. 6,149,620 and U.S. Pat. No. 7,678,069 can be highly effective in volumetric removal of soft tissue in the knee and elsewhere but are ineffective in resecting bone.

Therefore, the need exists for tools that can effectively remove both bone and soft tissue and which can combine the advantages of both cutter-based hard tissue resection and RF-based soft tissue ablation. At least some of these objectives will be met by the inventions described below.

SUMMARY OF THE INVENTION

The present invention provides a variety of improved tissue removal devices and methods, including devices and methods which can remove tissue by cutting (resection) and/or by radiofrequency (RF) ablation.

In a first specific aspect of the present invention, a medical device for removing tissue includes an elongated sleeve having a longitudinal axis, a proximal end, and a distal end. A ceramic cutting member with at least one cutting edge extends distally from the distal end of the elongated sleeve, and an electrode is carried by the cutting member. A motor drive is configured to couple to the proximal end of elongated sleeve to rotate the cutting member. In some embodiments, the elongated sleeve is an inner sleeve and is coaxially and rotatably disposed in an outer sleeve, where the outer sleeve may have a cut-out to expose the ceramic cutting member and the electrode.

The cutting edge of medical device for removing tissue will have a radially outward rotational periphery which is at least as great as an outward rotational periphery of the electrode, and the dielectric material typically comprises a wear-resistant ceramic material, usually consisting exclusively of the wear-resistant ceramic material. Exemplary wear-resistant ceramic materials are selected from the group consisting of yttria-stabilized zirconia, magnesia-stabilized zirconia, ceria-stabilized zirconia, zirconia toughened alumina and silicon nitride. The medical device will typically further comprise an RF source connected to the electrode and a controller operatively connectable to the motor drive, the RF source, and a negative pressure source.

The cutting member of the medical device will often have at least one window in a side thereof which communicates with an interior channel of the elongated (inner) sleeve which is configured to be connected to a negative pressure source. The window is typically adjacent to the electrode so that material released by resection and/or ablation can be aspirated through said window. The window optionally can be used for fluid infusion for use in electrosurgery. In some instances, the window is proximal to the electrode and/or proximal to the cutting edges, an/or at least partly intermediate the cutting edges. The cutting member may have from 1 to 100 cutting edges, a diameter ranging between 2 mm and 10 mm, and may extend over an axial length ranging between 1 mm and 10 mm. The cutting edges may be arranged in a pattern selected from at least one of helical, angled and straight relative to said axis.

In a second specific aspect of the present invention, a medical system for removing tissue includes an elongated rotatable shaft with a distal tip comprising (or composed of) a ceramic material. A motor drive is configured to rotate the shaft and the distal tip, and an electrode is carried by the distal tip. The electrode is coupled to an RF source, and a controller is operatively connected to the motor drive and to the RF source. The controller is configured to stop rotation of the shaft in a selected position, such as a position that will expose the electrode in a position that allows it to be used for ablative or other tissue treatment.

The medical device may further include a sensor configured to sense a rotational position of the shaft and to send signals to the controller indicating said rotational position. The controller may be configured to stop rotation of the shaft in the selected or other position, for example when a portion of distal tip such as the electrode or cutter element is properly oriented to perform a desired ablation, resection, or other treatment. The sensor is usually a Hall sensor. The controller may be further configured to control delivery of RF energy to the electrode when the shaft in said selected position. The distal tip of the rotatable shaft may have at least one window in a side thereof that opens to an interior channel in the shaft where the channel is configured to communicate with a negative pressure source. The window may be adjacent the electrode and/or may be at least partly proximal to the electrode. The distal tip may comprise or consist entirely of a wear-resistant ceramic material, such as those listed elsewhere herein.

In a third specific aspect of the present invention, a medical device for removing tissue includes an elongated shaft with a distal tip having a ceramic member. A window in the ceramic member connects to an interior channel in the shaft, and an electrode in the ceramic member is positioned adjacent to a distal end of the window. The interior channel is configured to be coupled to a negative pressure source.

The electrode may have a width equal to at least 50% of a width of the window, sometimes being at least 80% of the width of the window, and sometimes being at least 100% of the width of the window, or greater. At least one side of the window may have a sharp edge, and the electrode may at least partly encircle the distal end of the window. The ceramic member may have at least one sharp edge for cutting tissue, and a radially outward surface of the ceramic member usually defines a cylindrical periphery with an outward surface of the electrode being within said cylindrical periphery. The ceramic member will usually have at least one and more usually a plurality of sharp edges for cutting tissue.

In a fourth specific aspect of the present invention, a method for electrosurgical tissue ablation comprises providing an elongated shaft with a working end including an active electrode carried adjacent to a window that opens to an interior channel in the shaft. The channel is connected to a negative pressure source, and the active electrode and window are positioned in contact with target tissue in a fluid-filled space. The negative pressure source may be activated to suction the target tissue into the window, and the active electrode is activated (typically to deliver RF energy) to ablate tissue while translating the working end relative to the targeted tissue.

In specific aspects of the methods, a motor drive rotates the shaft and the distal tip (typically at at least 3,000 rpm), and a controller operatively connects the interior channel to the negative pressure source and an RF source to the electrode. The ceramic member is a wear-resistant material, typically as noted previously herein. Tissue debris is aspirated through the interior channel, and the working end is translated to remove a surface portion of the targeted tissue. and/or to undercut the targeted tissue to thereby remove chips of tissue.

In still further aspects, the present invention provides a high-speed rotating cutter or burr that is fabricated entirely of a ceramic material. In one variation, the ceramic is a molded monolith with sharp cutting edges and is adapted to be motor driven at speeds ranging from 3,000 rpm to 20,000 rpm. The ceramic cutting member is coupled to an elongate inner sleeve that is configured to rotate within a metal, ceramic or composite outer sleeve. The ceramic material is exceptionally hard and durable and will not fracture and thus not leave foreign particles in a treatment site. In one aspect, the ceramic has a hardness of at least 8 GPa ($kg/mm^2$) and a fracture toughness of at least 2 $MPam^{1/2}$. The "hardness" value is measured on a Vickers scale and "fracture toughness" is measured in $MPam^{1/2}$. Fracture toughness refers to a property which describes the ability of a material containing a flaw to resist further fracture and expresses a material's resistance to such fracture. In another aspect, it has been found that materials suitable for the cutting member of the invention have a certain hardness-to-fracture toughness ratio, which is a ratio of at least 0.5 to 1

While the cutting assembly and ceramic cutting member of the invention have been designed for arthroscopic procedures, such devices can be fabricated in various cross-sections and lengths and can be use in other procedures for cutting bone, cartilage and soft tissue such as in ENT procedures, spine and disc procedures and plastic surgeries.

In another aspect, the present invention provides a medical device that includes an elongated sleeve having a longitudinal axis, a proximal end and a distal end. A cutting member extends distally from the distal end of the elongated sleeve, and has sharp cutting edges. The cutting head is formed from a wear-resistant ceramic material, and a motor coupled to the proximal end of elongated sleeve rotates the cutting member. The cutter may be engaged against bone and rotated to cut bone tissue without leaving any foreign particles in the site.

The wear-resistant ceramic material may comprise any one or combination of (1) zirconia, (2) a material selected from the group of yttria-stabilized zirconia, magnesia-stabilized zirconia and zirconia toughened alumina, or (3) silicon nitride. The cutting member typically has from 2 to 100 cutting edges, a cylindrical periphery, and is usually rounded in the distal direction. The cutting member will typically have diameter ranging from 2 mm to 10 mm, and the cutting edges will typically extend over an axial length ranging between 1 mm and 10 mm. The cutting edges may be any one of helical, angled or straight relative to said axis, and flutes between the cutting edges usually have a depth ranging from 0.10 mm to 2.5 mm. An aspiration tube may be configured to connect to a negative pressure source, where the cutting member has at least one window in a side thereof which opens to a hollow interior. In these embodiments, the hollow interior is open to a central passage of the elongated member which is connected to the aspiration tube.

In a further aspect, the present invention provides a medical device for treating bone including an elongated shaft having a longitudinal axis, a proximal end, and a distal end. A monolithic cutting member fabricated of a material having a hardness of at least 8 GPa ($kg/mm^2$) is coupled to the distal end of the elongated shaft, and a motor is operatively connected to the proximal end of the shaft, said motor being configured to rotate the shaft at at least 3,000 rpm.

The material usually has a fracture toughness of at least 2 MPam$^{1/2}$, and further usually has a coefficient of thermal expansion of less than 10 ($1\times10^6$/° C.). The material typically comprises a ceramic selected from the group of yttria-stabilized zirconia, magnesia-stabilized zirconia, ceria-stabilized zirconia, zirconia toughened alumina and silicon nitride, and the cutting member typically has a cylindrical periphery and an at least partly rounded periphery in an axial direction.

In a still further aspect, the present invention provides a medical device for treating bone comprising a monolithic cutting member fabricated of a material having a hardness-to-fracture toughness ratio of at least 0.5:1, usually at least 0.8:1, and often at least 1:1.

In yet another aspect, the present invention provides a medical device for cutting tissue including a motor-driven shaft having a longitudinal axis, a proximal end, a distal end, and a lumen extending therebetween. A rotatable cutting member is fabricated entirely of a ceramic material and is operatively coupled to the distal end of the motor-driven shaft. At least one window in the cutting member communicates with the lumen in the shaft, and a negative pressure source is in communication with the lumen to remove cut tissue from an operative site.

The ceramic material typically has a hardness of at least 8 GPa (kg/mm$^2$) and a fracture toughness of at least 2 MPam$^{1/2}$. Additionally, the ceramic material will usually have a coefficient of thermal expansion of less than 10 ($1\times10^6$/° C.). Exemplary ceramic materials are selected from the group consisting of yttria-stabilized zirconia, magnesia-stabilized zirconia, ceria-stabilized zirconia, zirconia toughened alumina and silicon nitride, and the cutting member usually has cutting edges where the at least one window is proximate to the cutting edges, and the at least one window is in at least one flute between the cutting edges.

In another aspect, the present invention provides a method for preventing foreign particle induced inflammation at a bone treatment site. A rotatable cutter fabricated of a ceramic material having a hardness of at least 8 GPa (kg/mm$^2$) and a fracture toughness of at least 2 MPam$^{1/2}$ is engaged against bone and rotated to cut bone tissue without leaving any foreign particles in the site.

The ceramic material is usually selected from the group consisting of yttria-stabilized zirconia, magnesia-stabilized zirconia, ceria-stabilized zirconia, zirconia toughened alumina and silicon nitride, and the cutter is typically rotated at 10,000 rpm or greater. Cut bone tissue is removed from the bone treatment site through a channel in the cutter, typically by aspirating the cut bone tissue through the channel.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to bone cutting and removal devices and related methods of use. Several variations of the invention will now be described to provide an overall understanding of the principles of the form, function and methods of use of the devices disclosed herein. In general, the present disclosure provides for an arthroscopic cutter or burr assembly for cutting or abrading bone that is disposable and is configured for detachable coupling to a non-disposable handle and motor drive component. This description of the general principles of this invention is not meant to limit the inventive concepts in the appended claims.

In general, the present invention provides a high-speed rotating ceramic cutter or burr that is configured for use in many arthroscopic surgical applications, including but not limited to treating bone in shoulders, knees, hips, wrists, ankles and the spine. More in particular, the device includes a cutting member that is fabricated entirely of a ceramic material that is extremely hard and durable, as described in detail below. A motor drive is operatively coupled to the ceramic cutter to rotate the burr edges at speeds ranging from 3,000 rpm to 20,000 rpm.

Figure 1:
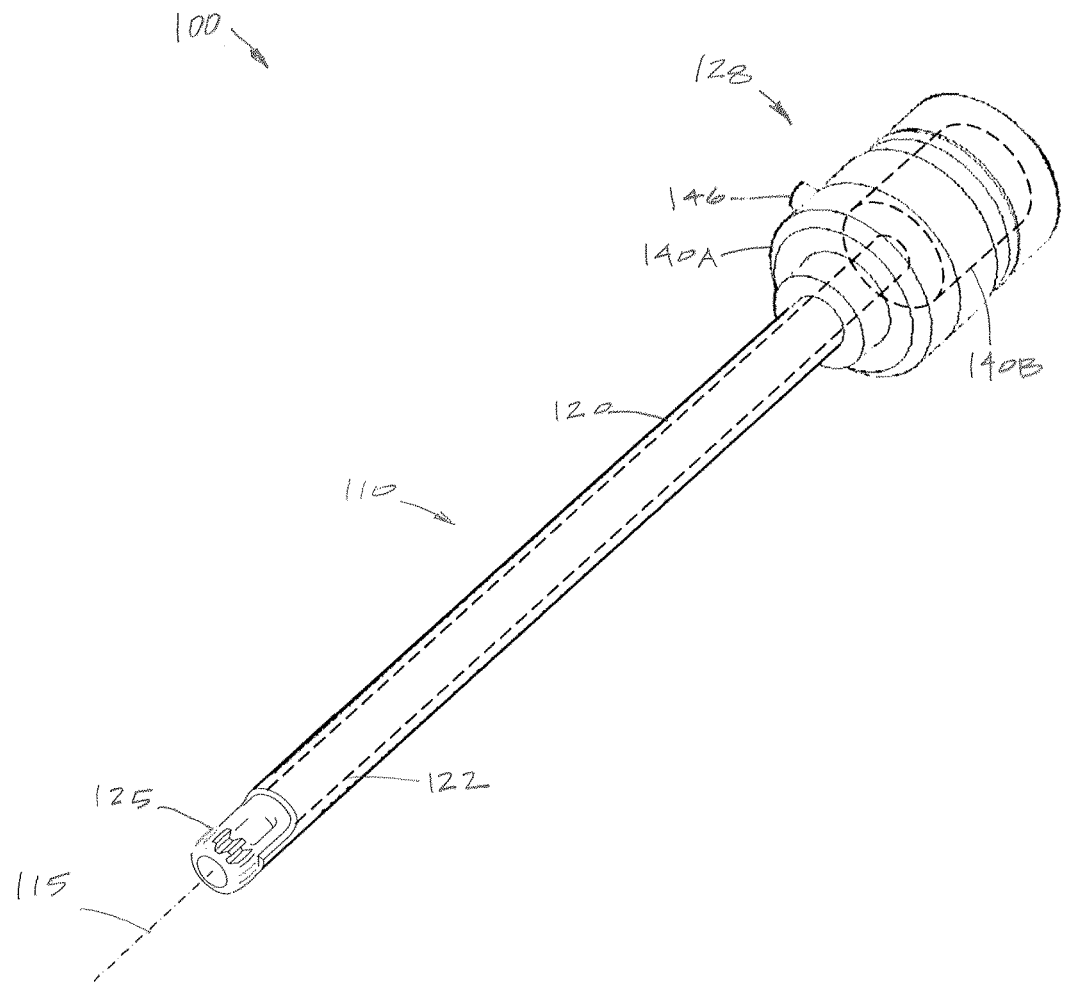
FIG. 1 is a perspective view of a disposable arthroscopic cutter or burr assembly with a ceramic cutting member carried at the distal end of a rotatable inner sleeve with a window in the cutting member proximal to the cutting edges of the burr.
Figure 2:
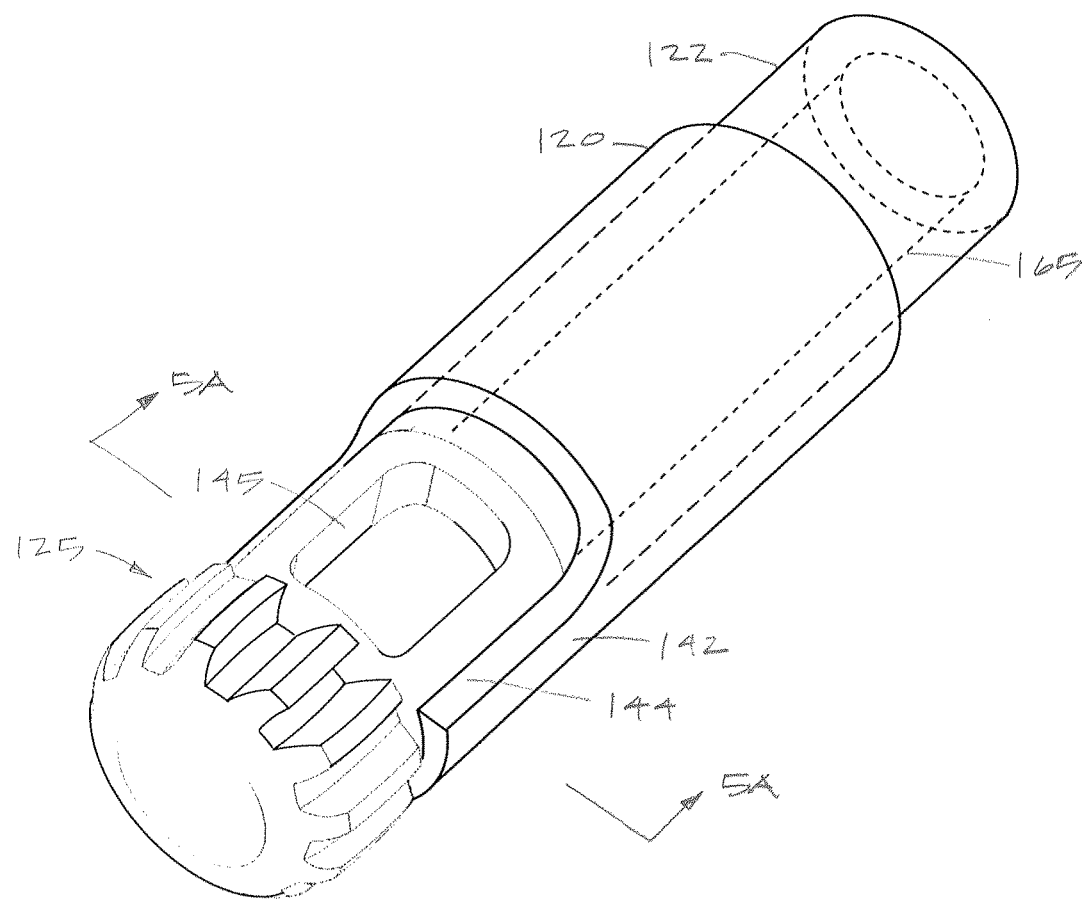
FIG. 2 is an enlarged perspective view of the ceramic cutting member of the arthroscopic cutter or burr assembly of FIG. 1.

In one variation shown in FIGS. 1-2, an arthroscopic cutter or burr assembly 100 is provided for cutting and removing hard tissue, which operates in an manner similar to commercially available metals shavers and burrs. FIG. 1 shows disposable burr assembly 100 that is adapted for detachable coupling to a handle 104 and motor drive unit 105 therein as shown in FIG. 3.

The cutter assembly 100 has a shaft 110 extending along longitudinal axis 115 that comprises an outer sleeve 120 and an inner sleeve 122 rotatably disposed therein with the inner sleeve 122 carrying a distal ceramic cutting member 125. The shaft 110 extends from a proximal hub assembly 128 wherein the outer sleeve 120 is coupled in a fixed manner to an outer hub 140A which can be an injection molded plastic, for example, with the outer sleeve 120 insert molded therein. The inner sleeve 122 is coupled to an inner hub 140B (phantom view) that is configured for coupling to the motor drive unit 105 (FIG. 3). The outer and inner sleeves 120 ands 122 typically can be a thin wall stainless steel tube, but other materials can be used such as ceramics, metals, plastics or combinations thereof.

Referring to FIG. 2, the outer sleeve 120 extends to distal sleeve region 142 that has an open end and cut-out 144 that is adapted to expose a window 145 in the ceramic cutting member 125 extending distally from the inner sleeve 122 during a portion of the inner sleeve's rotation. Referring to FIGS. 1 and 3, the proximal hub 128 of the burr assembly 100 is configured with a J-lock, snap-fit feature, screw thread or other suitable feature for detachably locking the hub assembly 128 into the handle 104 (FIG. 3). As can be seen in FIG. 1, the outer hub 140A includes a projecting key 146 that is adapted to mate with a receiving J-lock slot 148 in the handle 104 (see FIG. 3).

Figure 3:
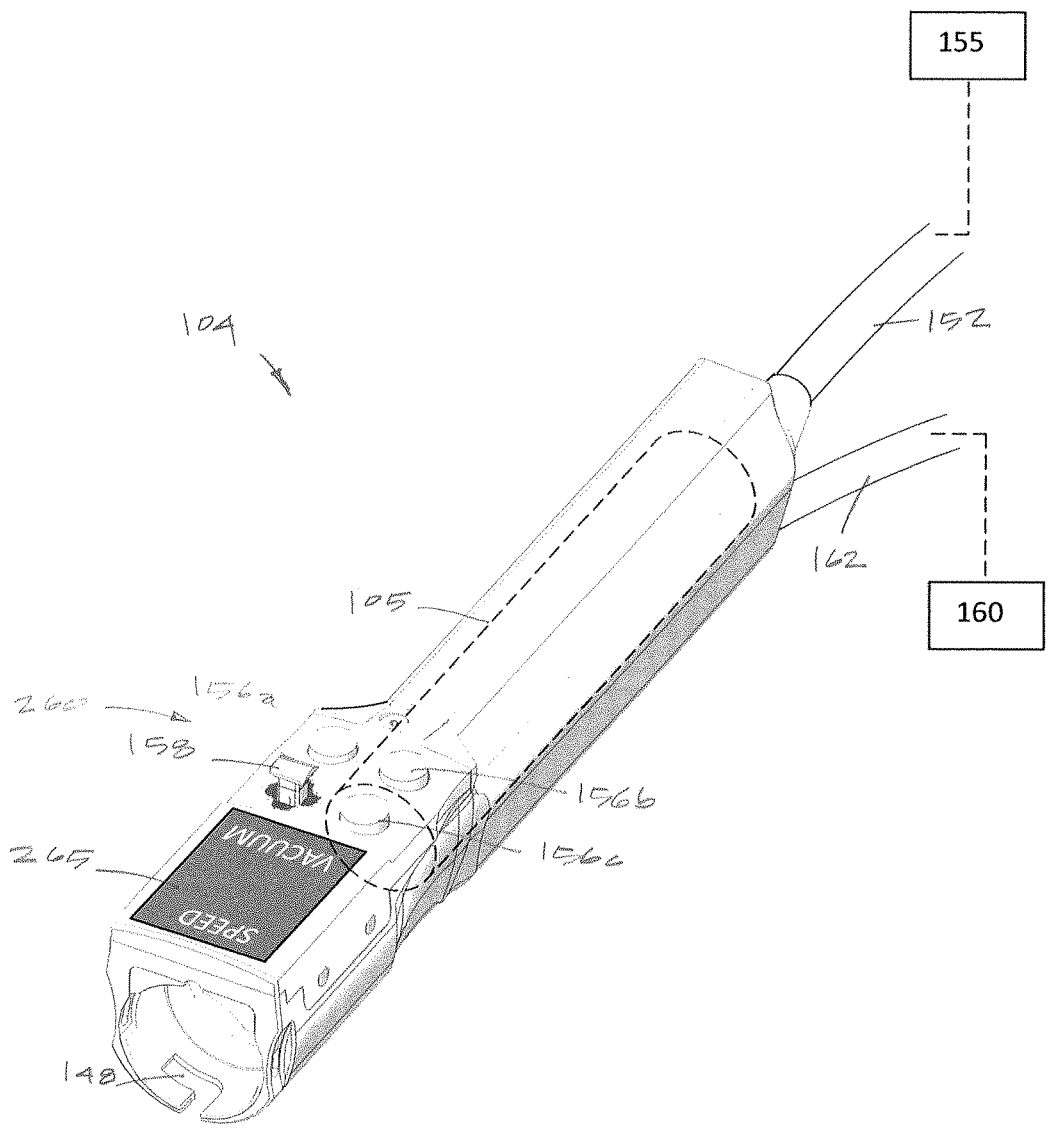
FIG. 3 is a perspective view of a handle body with a motor drive unit to which the burr assembly of FIG. 1 can be coupled, with the handle body including an LCD screen for displaying operating parameters of device during use together with a joystick and mode control actuators on the handle.

In FIG. 3, it can be seen that the handle 104 is operatively coupled by electrical cable 152 to a controller 155 which controls the motor drive unit 105. Actuator buttons 156a, 156b or 156c on the handle 104 can be used to select operating modes, such as various rotational modes for the ceramic cutting member. In one variation, a joystick 158 is moved forward and backward to adjust the rotational speed of the ceramic cutting member 125. The rotational speed of the cutter can continuously adjustable, or can be adjusted in increments up to 20,000 rpm. FIG. 3 further shows that negative pressure source 160 is coupled to aspiration tubing 162 which communicates with a flow channel in the handle 104 and lumen 165 in inner sleeve 122 which extends to window 145 in the ceramic cutting member 125 (FIG. 2).

Figure 4:
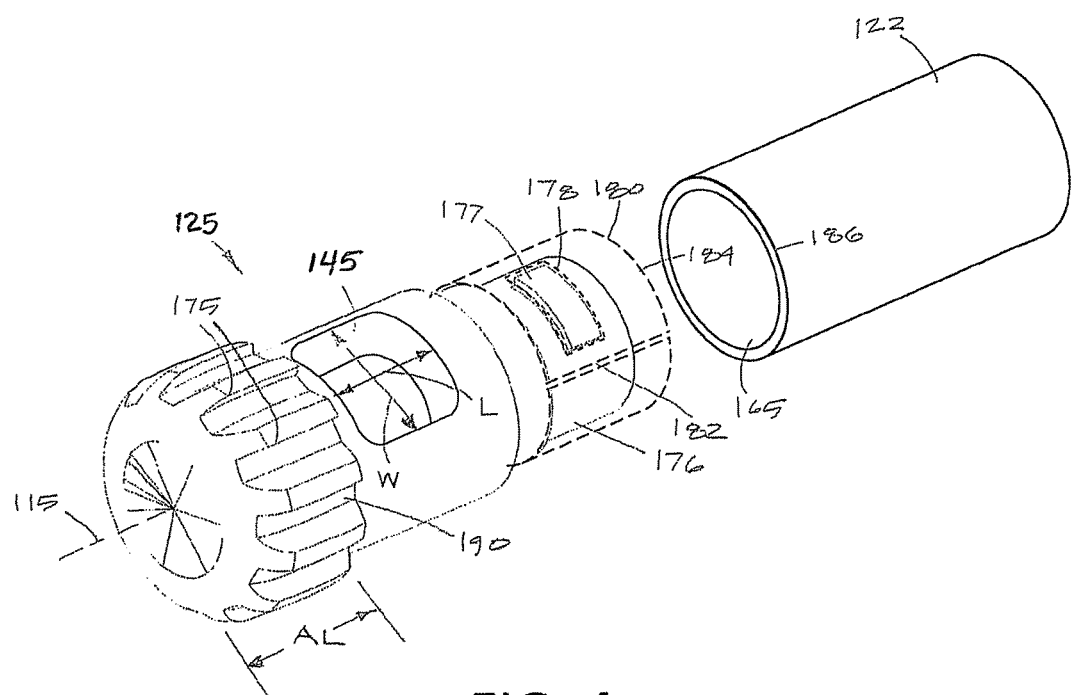
FIG. 4 is an enlarged perspective view of the ceramic cutting member showing a manner of coupling the cutter to a distal end of the inner sleeve of the burr assembly.

Now referring to FIGS. 2 and 4, the cutting member 125 comprises a ceramic body or monolith that is fabricated entirely of a technical ceramic material that has a very high hardness rating and a high fracture toughness rating, where "hardness" is measured on a Vickers scale and "fracture toughness" is measured in $MPam^{1/2}$. Fracture toughness refers to a property which describes the ability of a material containing a flaw or crack to resist further fracture and expresses a material's resistance to brittle fracture. The occurrence of flaws is not completely avoidable in the fabrication and processing of any components.

The authors evaluated technical ceramic materials and tested prototypes to determine which ceramics are best suited for the non-metal cutting member 125. When comparing the material hardness of the ceramic cutters of the invention to prior art metal cutters, it can easily be understood why typical stainless steel bone burrs are not optimal. Types 304 and 316 stainless steel have hardness ratings of 1.7 and 2.1, respectively, which is low and a fracture toughness ratings of 228 and 278, respectively, which is very high. Human bone has a hardness rating of 0.8, so a stainless steel cutter is only about 2.5 times harder than bone. The high fracture toughness of stainless steel provides ductile behavior which results in rapid cleaving and wear on sharp edges of a stainless steel cutting member. In contrast, technical ceramic materials have a hardness ranging from approximately 10 to 15, which is five to six times greater than stainless steel and which is 10 to 15 times harder than cortical bone. As a result, the sharp cutting edges of a ceramic remain sharp and will not become dull when cutting bone. The fracture toughness of suitable ceramics ranges from about 5 to 13 which is sufficient to prevent any fracturing or chipping of the ceramic cutting edges. The authors determined that a hardness-to-fracture toughness ratio ("hardness-toughness ratio") is a useful term for characterizing ceramic materials that are suitable for the invention as can be understood form the Chart A below, which lists hardness and fracture toughness of cortical bone, a 304 stainless steel, and several technical ceramic materials.

Chart A

| (GPa) | Hardness | Fracture Toughness ($MPam^{1/2}$) | Ratio Hardness to Fracture Toughness |
|---|---|---|---|
| Cortical bone | 0.8 | 12 | .07:1 |
| Stainless steel 304 | 2.1 | 228 | .01:1 |
| Yttria-stabilized zirconia (YTZP) | | | |
| YTZP 2000 (Superior Technical Ceramics) | 12.5 | 10 | 1.25:1 |
| YTZP 4000 (Superior Technical Ceramics) | 12.5 | 10 | 1.25:1 |
| YTZP (CoorsTek) | 13.0 | 13 | 1.00:1 |
| Magnesia stabilized zirconia (MSZ) | | | |

-continued

Chart A

| (GPa) | Hardness | Fracture Toughness (MPam$^{1/2}$) | Ratio Hardness to Fracture Toughness |
|---|---|---|---|
| Dura-Z ® (Superior Technical Ceramics) | 12.0 | 11 | 1.09:1 |
| MSZ 200 (CoorsTek) Zirconia toughened alumina (ZTA) | 11.7 | 12 | 0.98:1 |
| YTA-14 (Superior Technical Ceramics) | 14.0 | 5 | 2.80:1 |
| ZTA (CoorsTek) Ceria stabilized zirconia | 14.8 | 6 | 2.47:1 |
| CSZ (Superior Technical Ceramics) Silicon Nitride | 11.7 | 12 | 0.98:1 |
| SiN (Superior Technical Ceramics) | 15.0 | 6 | 2.50:1 |

As can be seen in Chart A, the hardness-toughness ratio for the listed ceramic materials ranges from 98× to 250× greater than the hardness-toughness ratio for stainless steel 304. In one aspect of the invention, a ceramic cutter for cutting hard tissue is provided that has a hardness-toughness ratio of at least 0.5:1, 0.8:1 or 1:1.

In one variation, the ceramic cutting member 125 is a form of zirconia. Zirconia-based ceramics have been widely used in dentistry and such materials were derived from structural ceramics used in aerospace and military armor. Such ceramics were modified to meet the additional requirements of biocompatibility and are doped with stabilizers to achieve high strength and fracture toughness. The types of ceramics used in the current invention have been used in dental implants, and technical details of such zirconia-based ceramics can be found in Volpato, et al., "Application of Zirconia in Dentistry: Biological, Mechanical and Optical Considerations", Chapter 17 in *Advances in Ceramics— Electric and Magnetic Ceramics, Bioceramics, Ceramics and Environment* (2011).

In one variation, the ceramic cutting member 125 is fabricated of an yttria-stabilized zirconia as is known in the field of technical ceramics, and can be provided by CoorsTek Inc., 16000 Table Mountain Pkwy., Golden, Colo. 80403 or Superior Technical Ceramics Corp., 600 Industrial Park Rd., St. Albans City, Vt. 05478. Other technical ceramics that may be used consist of magnesia-stabilized zirconia, ceria-stabilized zirconia, zirconia toughened alumina and silicon nitride. In general, in one aspect of the invention, the monolithic ceramic cutting member 125 has a hardness rating of at least 8 GPa (kg/mm$^2$). In another aspect of the invention, the ceramic cutting member 125 has a fracture toughness of at least 2 MPam$^{1/2}$.

The fabrication of such ceramics or monoblock components are known in the art of technical ceramics, but have not been used in the field of arthroscopic or endoscopic cutting or resecting devices. Ceramic part fabrication includes molding, sintering and then heating the molded part at high temperatures over precise time intervals to transform a compressed ceramic powder into a ceramic monoblock which can provide the hardness range and fracture toughness range as described above. In one variation, the molded ceramic member part can have additional strengthening through hot isostatic pressing of the part. Following the ceramic fabrication process, a subsequent grinding process optionally may be used to sharpen the cutting edges 175 of the burr (see FIGS. 2 and 4).

In FIG. 4, it can be seen that in one variation, the proximal shaft portion 176 of cutting member 125 includes projecting elements 177 which are engaged by receiving openings 178 in a stainless steel split collar 180 shown in phantom view. The split collar 180 can be attached around the shaft portion 176 and projecting elements 177 and then laser welded along weld line 182. Thereafter, proximal end 184 of collar 180 can be laser welded to the distal end 186 of stainless steel inner sleeve 122 to mechanically couple the ceramic body 125 to the metal inner sleeve 122. In another aspect of the invention, the ceramic material is selected to have a coefficient of thermal expansion between is less than 10 ($1 \times 10^6$/° C.) which can be close enough to the coefficient of thermal expansion of the metal sleeve 122 so that thermal stresses will be reduced in the mechanical coupling of the ceramic member 125 and sleeve 122 as just described. In another variation, a ceramic cutting member can be coupled to metal sleeve 122 by brazing, adhesives, threads or a combination thereof.

Referring to FIGS. 1 and 4, the ceramic cutting member 125 has window 145 therein which can extend over a radial angle of about 10° to 90° of the cutting member's shaft. In the variation of FIG. 1, the window is positioned proximally to the cutting edges 175, but in other variations, one or more windows or openings can be provided and such openings can extend in the flutes 190 (see FIG. 6) intermediate the cutting edges 175 or around a rounded distal nose of the ceramic cutting member 125. The length L of window 145 can range from 2 mm to 10 mm depending on the diameter and design of the ceramic member 125, with a width W of 1 mm to 10 mm.

Figure 6:
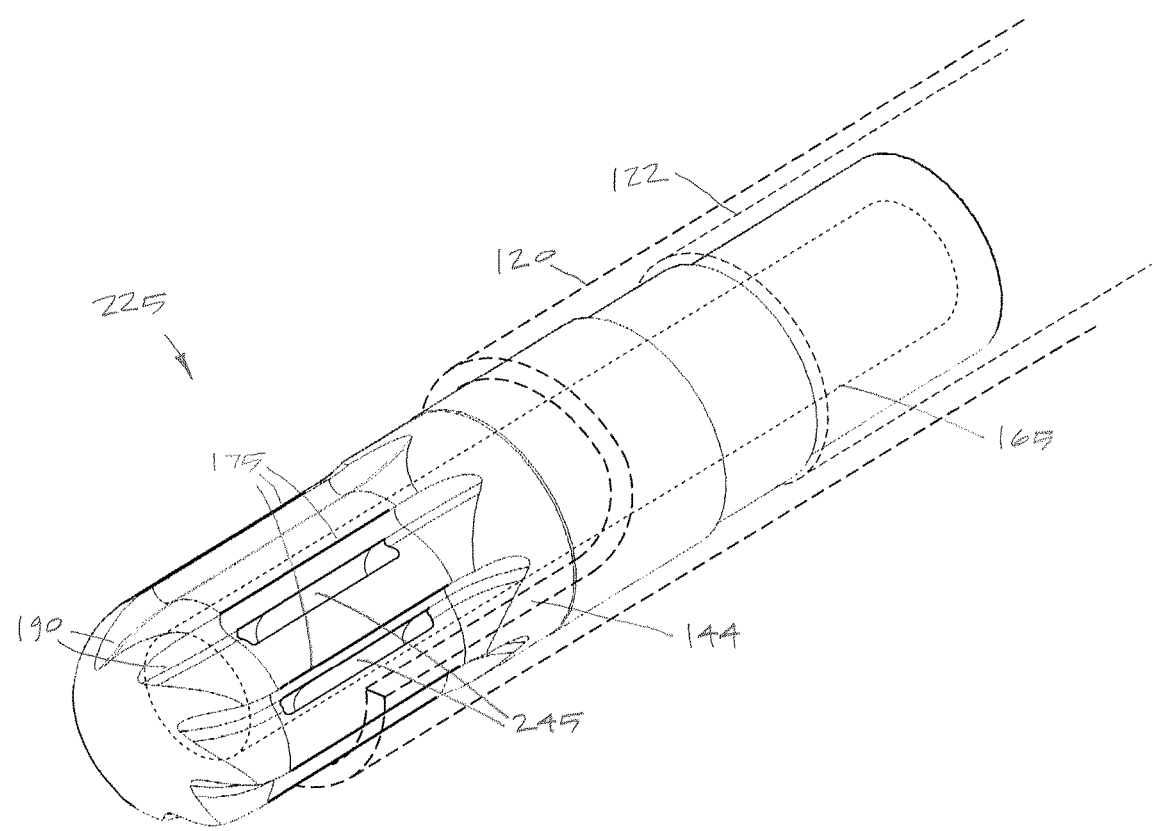
FIG. 6 is a perspective view of another ceramic cutting member carried at the distal end of an inner sleeve with a somewhat rounded distal nose and deeper flutes than the cutting member of FIGS. 2 and 4, and with aspiration openings or ports formed in the flutes.
Figure 7:
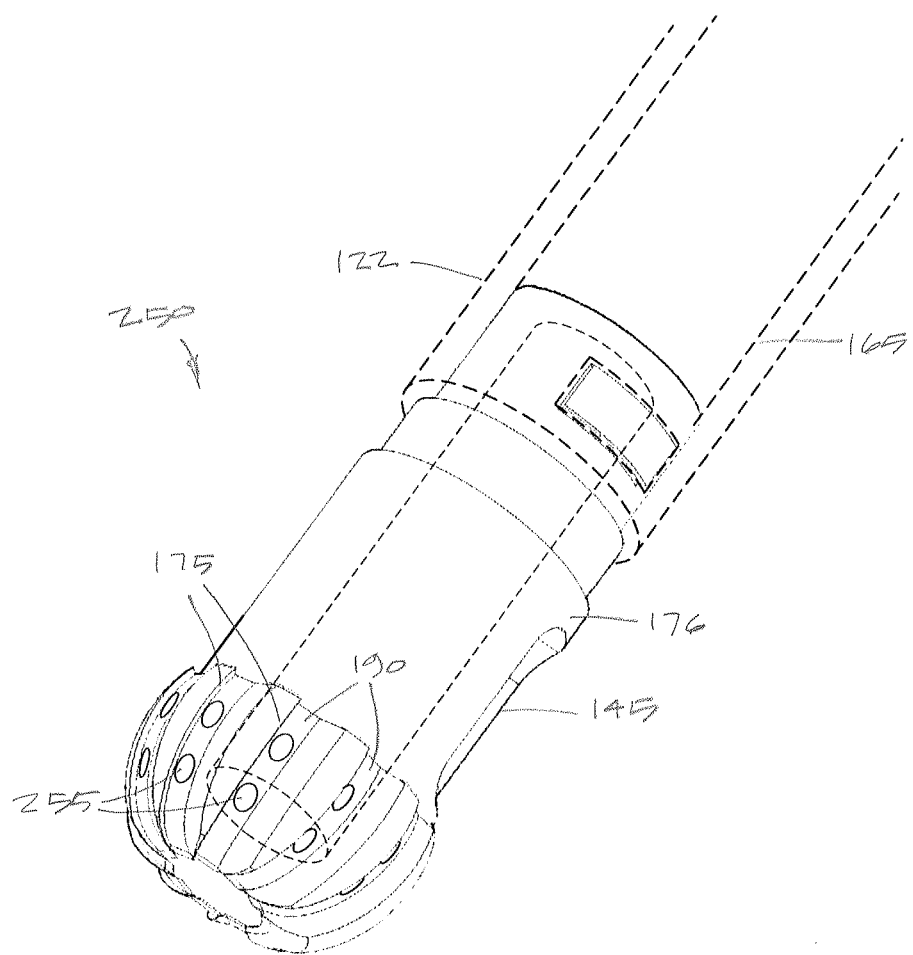
FIG. 7 is a perspective view of another ceramic cutting member with cutting edges that extend around a distal nose of the cutter together with an aspiration window in the shaft portion and aspiration openings in the flutes.

FIGS. 1 and 4 shows the ceramic burr or cutting member 125 with a plurality of sharp cutting edges 175 which can extend helically, axially, longitudinally or in a cross-hatched configuration around the cutting member, or any combination thereof. The number of cutting edges 175 ands intermediate flutes 190 can range from 2 to 100 with a flute depth ranging from 0.10 mm to 2.5 mm. In the variation shown in FIGS. 2 and 4, the outer surface or periphery of the cutting edges 175 is cylindrical, but such a surface or periphery can be angled relative to axis 115 or rounded as shown in FIGS. 6 and 7. The axial length AL of the cutting edges can range between 1 mm and 10 mm. While the cutting edges 175 as depicted in FIG. 4 are configured for optimal bone cutting or abrading in a single direction of rotation, it should be appreciated the that the controller 155 and motor drive 105 can be adapted to rotate the ceramic cutting member 125 in either rotational direction, or oscillate the cutting member back and forth in opposing rotational directions.

Figure 5A:
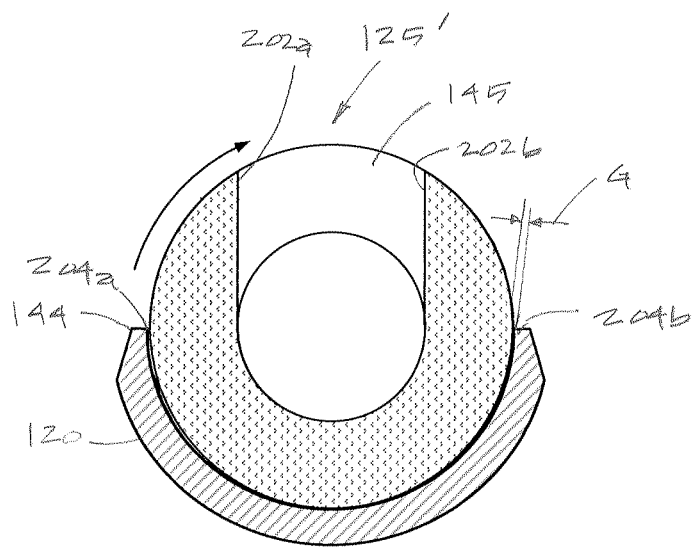
FIG. 5A is a cross-sectional view of a cutting assembly similar to that of FIG. 2 taken along line 5A-5A showing the close tolerance between sharp cutting edges of a window in a ceramic cutting member and sharp lateral edges of the outer sleeve which provides a scissor-like cutting effect in soft tissue.
Figure 5B:
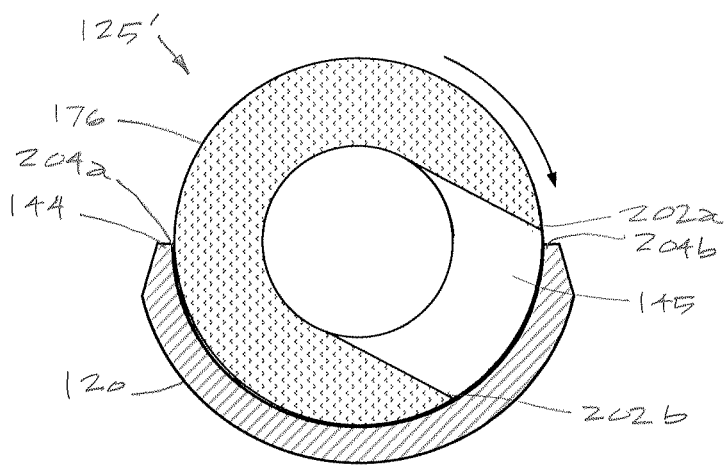
FIG. 5B is a cross-sectional view of the cutting assembly of FIG. 5A with the ceramic cutting member in a different rotational position than in FIG. 5A.

FIGS. 5A-5B illustrate a sectional view of the window 145 and shaft portion 176 of a ceramic cutting member 125' that is very similar to the ceramic member 125 of FIGS. 2 and 4. In this variation, the ceramic cutting member has window 145 with one or both lateral sides configured with sharp cutting edges 202a and 202b which are adapted to resect tissue when rotated or oscillated within close proximity, or in scissor-like contact with, the lateral edges 204a and 204b of the sleeve walls in the cut-out portion 144 of the distal end of outer sleeve 120 (see FIG. 2). Thus, in general, the sharp edges of window 145 can function as a cutter or shaver for resecting soft tissue rather than hard tissue or bone. In this variation, there is effectively no open gap G between the sharp edges 202a and 202b of the ceramic cutting member 125' and the sharp lateral edges 204a, 204b of the sleeve 120. In another variation, the gap G between the window cutting edges 202a, 202b and the sleeve edges 204a, 204b is less than about 0.020", or less than 0.010".

FIG. 6 illustrates another variation of ceramic cutting member 225 coupled to an inner sleeve 122 in phantom view. The ceramic cutting member again has a plurality of sharp cutting edges 175 and flutes 190 therebetween. The outer sleeve 120 and its distal opening and cut-out shape 144 are also shown in phantom view. In this variation, a plurality of windows or opening 245 are formed within the flutes 190 and communicate with the interior aspiration channel 165 in the ceramic member as described previously.

FIG. 7 illustrates another variation of ceramic cutting member 250 coupled to an inner sleeve 122 (phantom view) with the outer sleeve not shown. The ceramic cutting member 250 is very similar to the ceramic cutter 125 of FIGS. 1, 2 and 4, and again has a plurality of sharp cutting edges 175 and flutes 190 therebetween. In this variation, a plurality of windows or opening 255 are formed in the flutes 190 intermediate the cutting edges 175 and another window 145 is provided in a shaft portion 176 of ceramic member 225 as described previously. The openings 255 and window 145 communicate with the interior aspiration channel 165 in the ceramic member as described above.

It can be understood that the ceramic cutting members can eliminate the possibility of leaving metal particles in a treatment site. In one aspect of the invention, a method of preventing foreign particle induced inflammation in a bone treatment site comprises providing a rotatable cutter fabricated of a ceramic material having a hardness of at least 8 GPa (kg/mm$^2$) and/or a fracture toughness of at least 2 MPam$^{1/2}$ and rotating the cutter to cut bone without leaving any foreign particles in the treatment site. The method includes removing the cut bone tissue from the treatment site through an aspiration channel in a cutting assembly.

Figure 8:
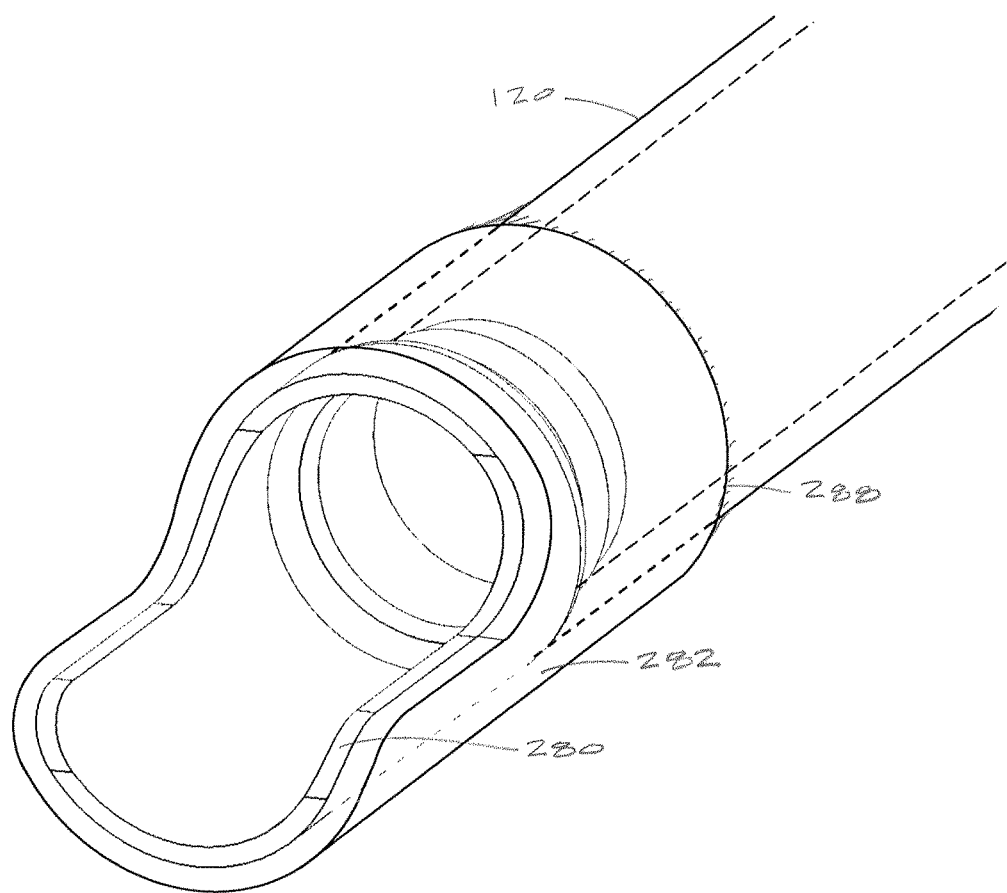
FIG. 8 is a perspective view of a ceramic housing carried at the distal end of the outer sleeve.

FIG. 8 illustrates variation of an outer sleeve assembly with the rotating ceramic cutter and inner sleeve not shown. In the previous variations, such as in FIGS. 1, 2 and 6, shaft portion 176 of the ceramic cutter 125 rotates in a metal outer sleeve 120. FIG. 8 illustrates another variation in which a ceramic cutter (not shown) would rotate in a ceramic housing 280. In this variation, the shaft or a ceramic cutter would thus rotate is a similar ceramic body which may be advantageous when operating a ceramic cutter at high rotational speeds. As can be seen in FIG. 8, a metal distal metal housing 282 is welded to the outer sleeve 120 along weld line 288. The distal metal housing 282 is shaped to support and provide strength to the inner ceramic housing 282.

Figure 9:
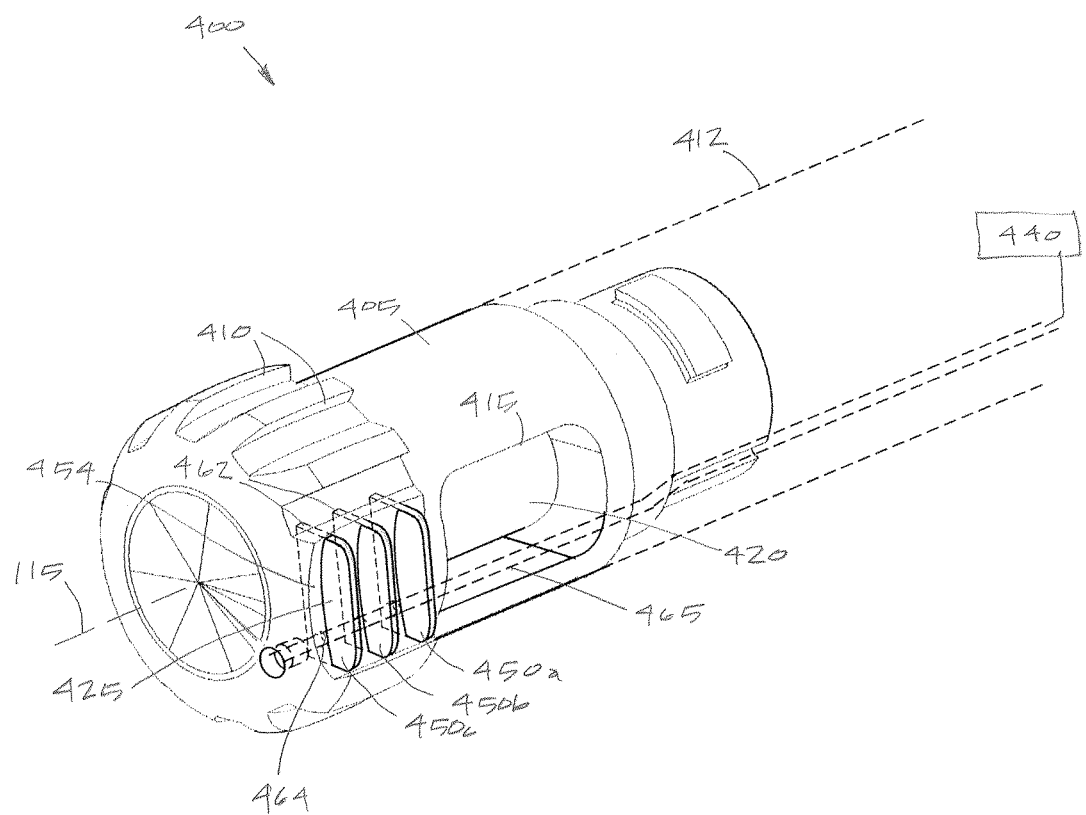
FIG. 9 is a perspective of another variation of a ceramic member with cutting edges that includes an aspiration window and an electrode arrangement positioned distal to the window.
Figure 10:
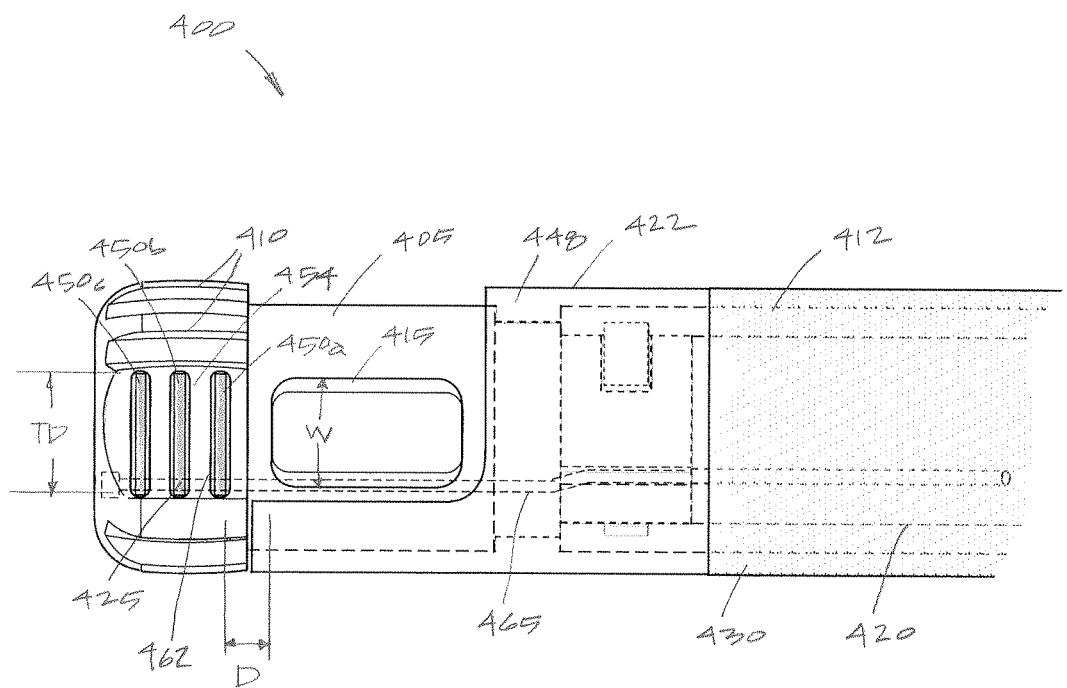
FIG. 10 is an elevational view of a ceramic member and shaft of FIG. 9 showing the width and position of the electrode arrangement in relation to the window.
Figure 11:
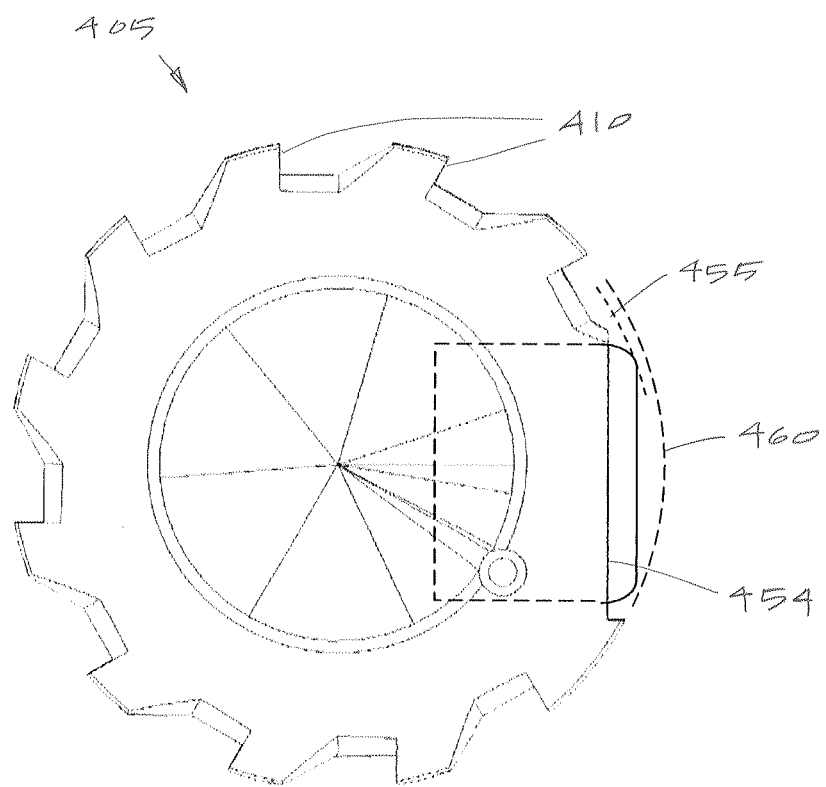
FIG. 11 is an end view of a ceramic member of FIGS. 9-10 the outward periphery of the electrode arrangement in relation to the rotational periphery of the cutting edges of the ceramic member.

FIGS. 9-11 are views of an alternative tissue resecting assembly or working end 400 that includes a ceramic or other dielectric member 405 with cutting edges 410 in a form similar to that described previously. FIG. 9 illustrates the monolithic ceramic member 405 carried as a distal tip of a shaft or inner sleeve 412 as described in previous embodiments. The ceramic member 405 again has a window 415 that communicates with aspiration channel 420 in shaft 412 that is connected to negative pressure source 160 as described previously. The inner sleeve 412 is operatively coupled to a motor drive 105 and rotates in an outer sleeve 422 of the type shown in FIG. 2. The outer sleeve 422 is shown in FIG. 10.

In the variation illustrated in FIG. 9, the ceramic member 405 carries an electrode arrangement 425, or active electrode, having a single polarity that is operatively connected to an RF source 440. A return electrode, or second polarity electrode 430, is provided on the outer sleeve 422 as shown in FIG. 10. In one variation, the outer sleeve 422 can comprise an electrically conductive material such as stainless steel to thereby function as return electrode 445, with a distal portion of outer sleeve 422 is optionally covered by a thin insulative layer 448 such as parylene, to space apart the active electrode 425 from the return electrode 430.

The active electrode arrangement 425 can consist of a single conductive metal element or a plurality of metal elements as shown in FIGS. 9 and 10. In one variation shown in FIG. 9, the plurality of electrode elements 450a, 450b and 450c extend transverse to the longitudinal axis 115 of ceramic member 405 and inner sleeve 412 and are slightly spaced apart in the ceramic member. In one variation shown in FIGS. 9 and 10, the active electrode 425 is spaced distance D from the distal edge 452 of window 415 which is less than 5 mm and often less than 2 mm for reasons described below. The width W and length L of window 415 can be the same as described in a previous embodiment with reference to FIG. 4.

As can be seen in FIGS. 9 and 11, the electrode arrangement 425 is carried intermediate the cutting edges 410 of the ceramic member 405 in a flattened region 454 where the cutting edges 410 have been removed. As can be best understood from FIG. 11, the outer periphery 455 of active electrode 425 is within the cylindrical or rotational periphery of the cutting edges 410 when they rotate. In FIG. 11, the rotational periphery of the cutting edges is indicated at 460. The purpose of the electrode's outer periphery 455 being equal to, or inward from, the cutting edge periphery 460 during rotation is to allow the cutting edges 410 to rotate at high RPMs to engage and cut bone or other hard tissue without the surface or the electrode 425 contacting the targeted tissue.

FIG. 9 further illustrates a method of fabricating the ceramic member 405 with the electrode arrangement 425 carried therein. The molded ceramic member 405 is fabricated with slots 462 that receive the electrode elements 450a-450c, with the electrode elements fabricated from stainless steel, tungsten or a similar conductive material. Each electrode element 450a-450c has a bore 464 extending therethrough for receiving an elongated wire electrode element 465. As can be seen in FIG. 9, and the elongated wire electrode 465 can be inserted from the distal end of the ceramic member 405 through a channel in the ceramic member 405 and through the bores 464 in the electrode elements 450a-450c. The wire electrode 465 can extend through the shaft 412 and is coupled to the RF source 440. The wire electrode element 465 thus can be used as a means of mechanically locking the electrode elements 450a-450c in slots 462 and also as a means to deliver RF energy to the electrode 425.

Another aspect of the invention is illustrated in FIGS. 9-10 wherein it can be seen that the electrode arrangement 425 has a transverse dimension TD relative to axis 115 that is substantial in comparison to the window width W as depicted in FIG. 10. In one variation, the electrode's transverse dimension TD is at least 50% of the window width W, or the transverse dimension TD is at least 80% of the window width W. In the variation of FIGS. 9-10, the electrode transverse dimension TD is 100% or more of the window width W. It has been found that tissue debris and byproducts from RF ablation are better captured and extracted by a window 415 that is wide when compared to the width of the RF plasma ablation being performed.

In general, the tissue resecting system comprises an elongated shaft with a distal tip comprising a ceramic member, a window in the ceramic member connected to an interior channel in the shaft and an electrode arrangement in the ceramic member positioned distal to the window and having a width that is at least 50% of the width W of the window, usually at least 80% of the width W of the window, and often at least 100% of the width W of the window, or greater. Further, the system includes a negative pressure source 160 in communication with the interior channel 420.

Figure 12A:
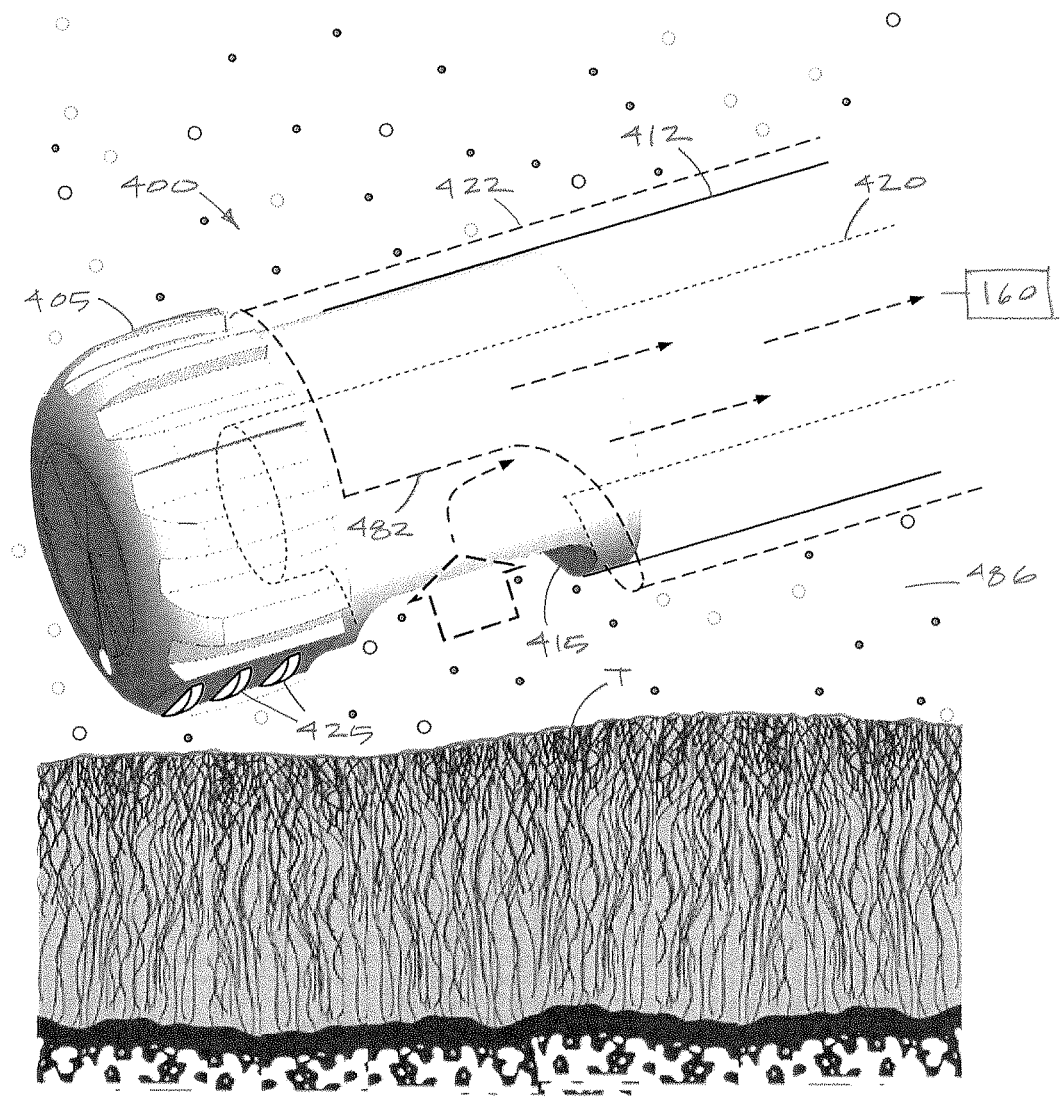
FIG. 12A is a schematic view of the working end and ceramic cutting member of FIGS. 9-11 illustrating a step in a method of use.
Figure 12B:
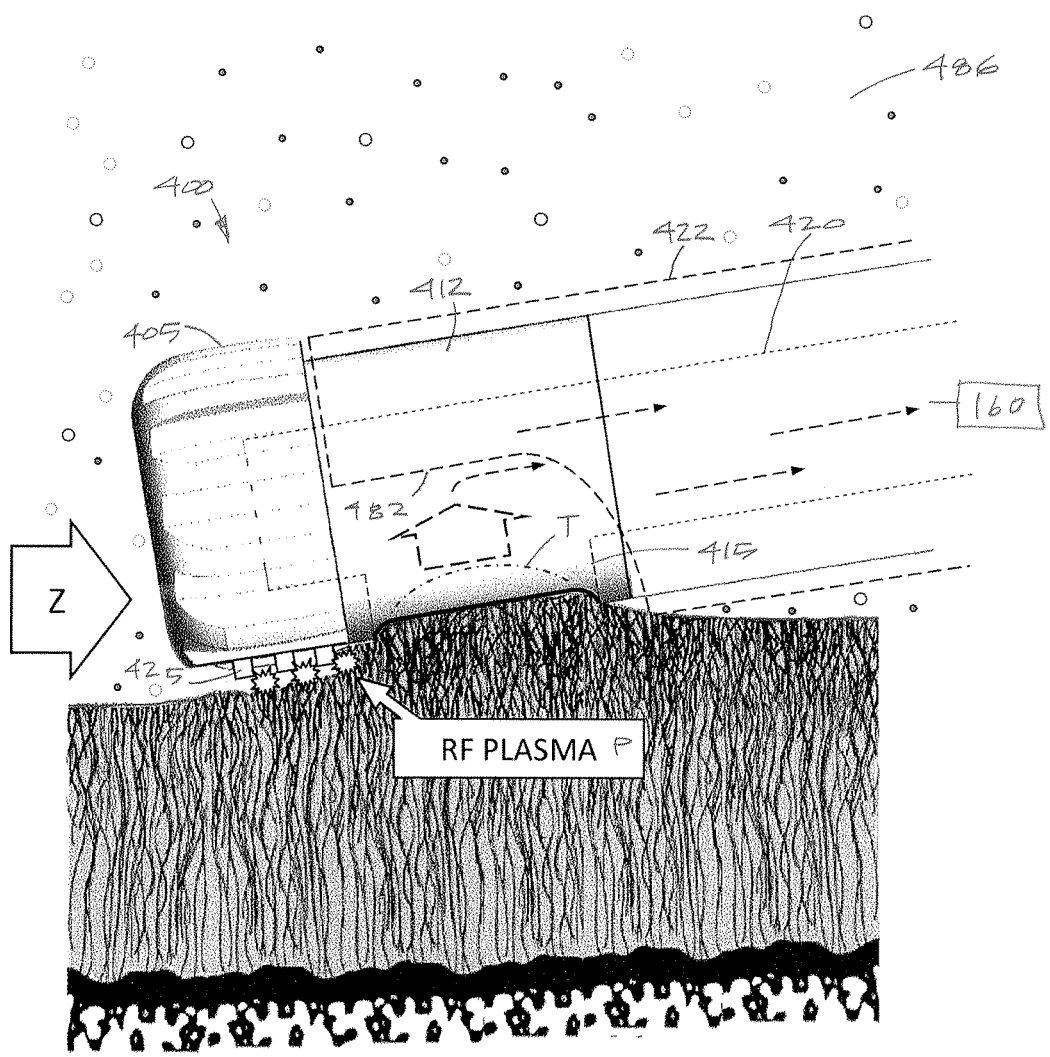
FIG. 12B is another view of the working end of FIG. 12A illustrating a subsequent step in a method of use to ablate a tissue surface.
Figure 12C:
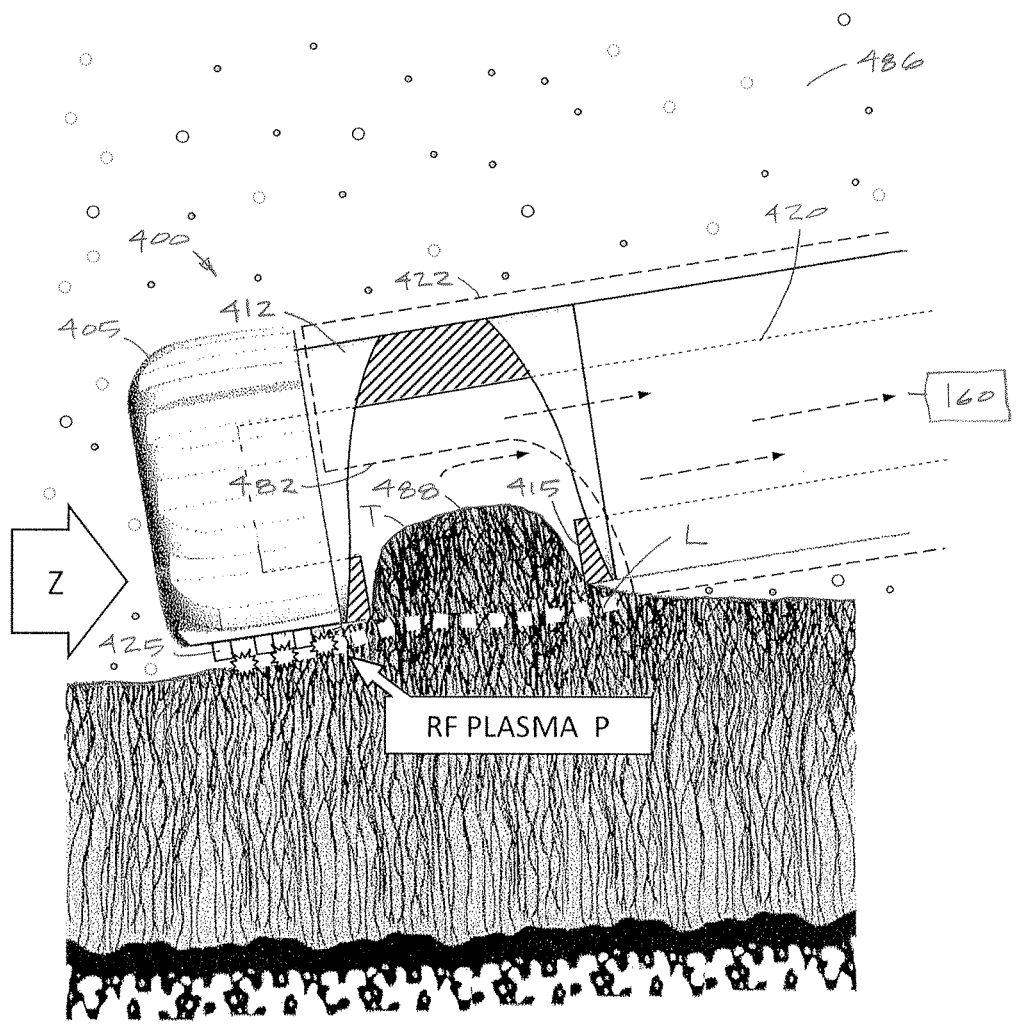
FIG. 12C is a view of the working end of FIG. 12A illustrating a method of tissue resection and aspiration of tissue chips to rapidly remove volumes of tissue.

Now turning to FIGS. 12A-12C, a method of use of the resecting assembly 400 of FIG. 9 can be explained. In FIG. 12A, the system and a controller is operated to stop rotation of the ceramic member 405 in a selected position were the window 415 is exposed in the cut-out 482 of the open end of outer sleeve 422 shown in phantom view. In one variation, a controller algorithm can be adapted to stop the rotation of the ceramic member 405 that uses a Hall sensor 484a in the handle 104 (see FIG. 3) that senses the rotation of a magnet 484b carried by inner sleeve hub 140B as shown in FIG. 2. The controller algorithm can receive signals from the Hall sensor which indicates a rotational position of the inner sleeve 412 and ceramic member 405 relative to the outer sleeve 422. The magnet 484b (FIG. 3) can be positioned in the hub 140B (FIG. 2) so that when sensed by the Hall sensor, the controller algorithm can de-activate the motor drive 105 so as to stop the rotation of the inner sleeve in any selected position, e.g. with the window 415 and cut-out 482 aligned.

Under endoscopic vision, referring to FIG. 12B, the physician then can position the electrode arrangement 425 in contact with tissue targeted T for ablation and removal in a working space filled with fluid 486, such as a saline solution which enables RF plasma creation about the electrode. The negative pressure source 160 is activated prior to or contemporaneously with the step of delivering RF energy to electrode 425. Still referring to FIG. 12B, when the ceramic member 405 is positioned in contact with tissue and translated in the direction of arrow Z, the negative pressure source 160 suctions the targeted tissue into the window 415. At the same time, RF energy delivered to electrode arrangement 425 creates a plasma P as is known in the art to thereby ablate tissue. The ablation then will be very close to the window 415 so that tissue debris, fragments, detritus and byproducts will be aspirated along with fluid 486 through the window 415 and outwardly through the interior extraction channel 420 to a collection reservoir. In one method shown schematically in FIG. 12B, a light movement or translation of electrode arrangement 425 over the targeted tissue will ablate a surface layer of the tissue and aspirate away the tissue detritus.

FIG. 12C schematically illustrates a variation of a method which is of particular interest. It has been found if suitable downward pressure on the working end 400 is provided, then axial translation of working end 400 in the direction arrow Z in FIG. 12C, together with suitable negative pressure and the RF energy delivery will cause the plasma P to undercut the targeted tissue along line L that is suctioned into window 415 and then cut and scoop out a tissue chips indicated at 488. In effect, the working end 400 then can function more as a high volume tissue resecting device instead of, or in addition to, its ability to function as a surface ablation tool. In this method, the cutting or scooping of such tissue chips 488 would allow the chips to be entrained in outflows of fluid 486 and aspirated through the extraction channel 420. It has been found that this system with an outer shaft diameter of 7.5 mm, can perform a method of the invention can ablate, resect and remove tissue at a rate greater than 15 grams/min, often greater than 20 grams/min, and sometimes greater than 25 grams/min.

In general, a method corresponding to the invention includes providing an elongated shaft with a working end 400 comprising an active electrode 425 carried adjacent to a window 415 that opens to an interior channel in the shaft which is connected to a negative pressure source, positioning the active electrode and window in contact with targeted tissue in a fluid-filled space, activating the negative pressure source to thereby suction targeted tissue into the window and delivering RF energy to the active electrode to ablate tissue while translating the working end across the targeted tissue. The method further comprises aspirating tissue debris through the interior channel 420. In a method, the working end 400 is translated to remove a surface portion of the targeted tissue. In a variation of the method, the working end 400 is translated to undercut the targeted tissue to thereby remove chips 488 of tissue.

Figure 13A:
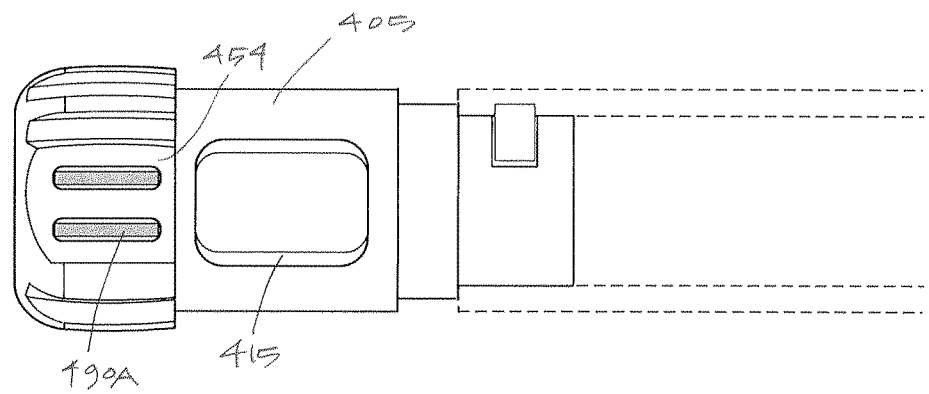
FIG. 13A is an elevational view of an alternative ceramic member and shaft similar to that of FIG. 9 illustrating an electrode variation.
Figure 13B:
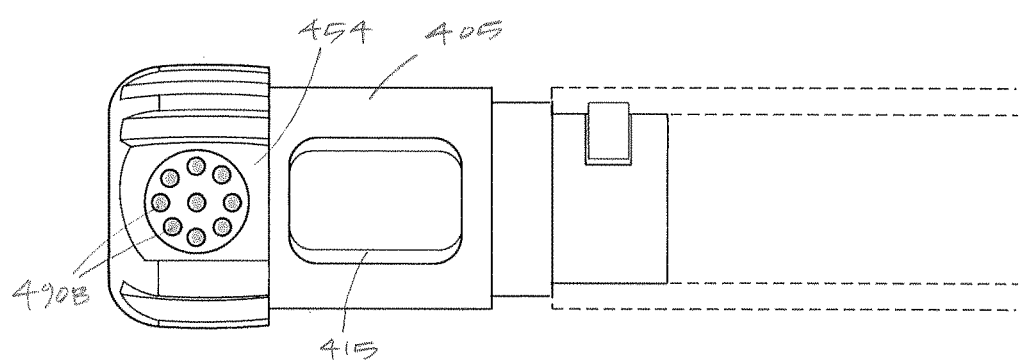
FIG. 13B is an elevational view of another ceramic member similar to that of FIG. 12A illustrating another electrode variation.
Figure 13C:
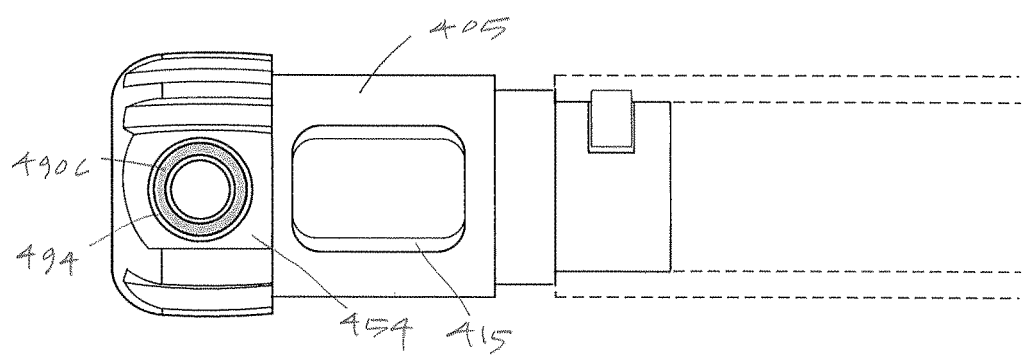
FIG. 13C is an elevational view of another ceramic member similar to that of FIGS. 12A-12B illustrating another electrode variation.

Now turning to FIGS. 13A-13C, other distal ceramic tips of cutting assemblies are illustrated that are similar to that of FIGS. 9-11, except the electrode configurations carried by the ceramic members 405 are varied. In FIG. 13A, the electrode 490A comprises one or more electrode elements extending generally axially distally from the window 415. FIG. 13B illustrates an electrode 490B that comprises a plurality of wire-like elements 492 projecting outwardly from surface 454. FIG. 13C shows electrode 490C that comprises a ring-like element that is partly recessed in a groove 494 in the ceramic body. All of these variations can produce an RF plasma that is effective for surface ablation of tissue, and are positioned adjacent to window 415 to allow aspiration of tissue detritus from the site.

Figure 14:
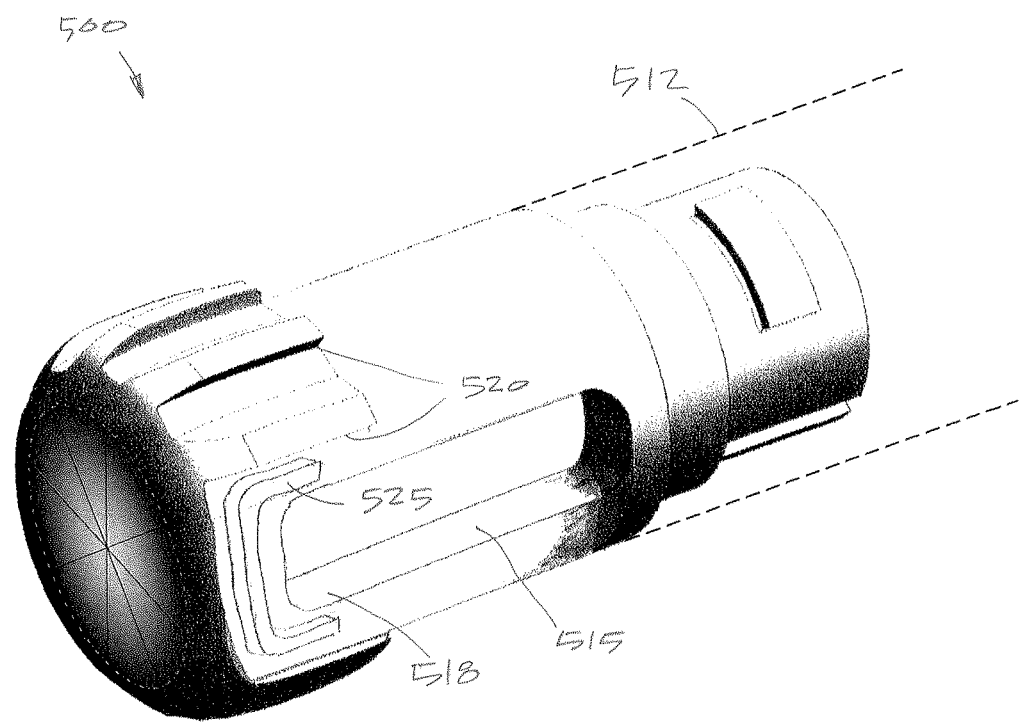
FIG. 14 is a perspective view of an alternative working end and ceramic cutting member with an electrode partly encircling a distal portion of an aspiration window.

FIG. 14 illustrates another variation of a distal ceramic tip 500 of an inner sleeve 512 that is similar to that of FIG. 9 except that the window 515 has a distal portion 518 that extends distally between the cutting edges 520, which is useful for aspirating tissue debris cut by high speed rotation of the cutting edges 520. Further, in the variation of FIG. 14, the electrode 525 encircles a distal portion 518 of window 515 which may be useful for removing tissue debris that is ablated by the electrode when the ceramic tip 500 is not rotated but translated over the targeted tissue as described above in relation to FIG. 12B. In another variation, a distal tip 500 as shown in FIG. 14 can be energized for RF ablation at the same time that the motor drive rotates back and forth (or oscillates) the ceramic member 500 in a radial arc ranging from 1° to 180° and more often from 10° to 90°.

Figure 15A:
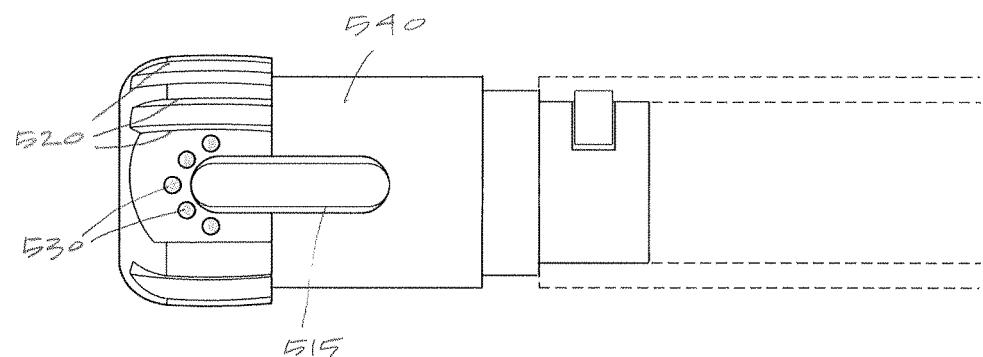
FIG. 15A is an elevational view of a working end variation with an electrode arrangement partly encircling a distal end of the aspiration window.
Figure 15B:
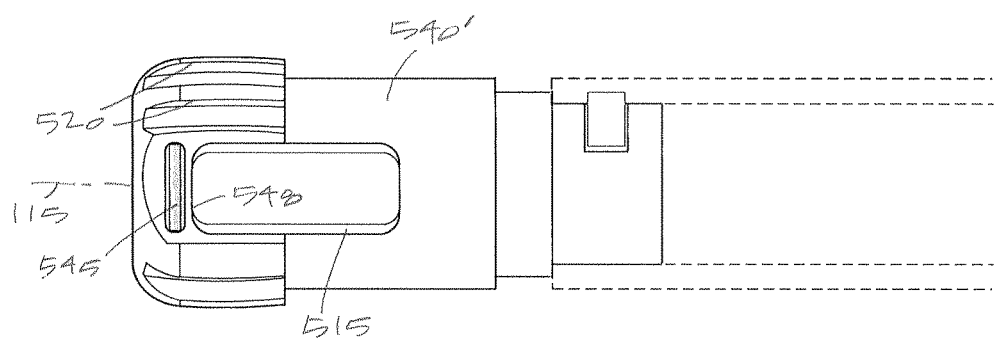
FIG. 15B is an elevational view of another working end variation with an electrode positioned adjacent a distal end of the aspiration window.

FIGS. 15A-15B illustrate other distal ceramic tips 540 and 540' that are similar to that of FIG. 14 except the electrode configurations differ. In FIG. 15A, the window 515 has a distal portion 518 that again extends distally between the cutting edges 520, with electrode 530 comprising a plurality of projecting electrode elements that extend partly around the window 515. FIG. 15B shows a ceramic tip 540' with window 515 having a distal portion 518 that again extends distally between the cutting edges 520. In this variation, the electrode 545 comprises a single blade element that extends transverse to axis 115 and is in close proximity to the distal end 548 of window 515.

Figure 16:
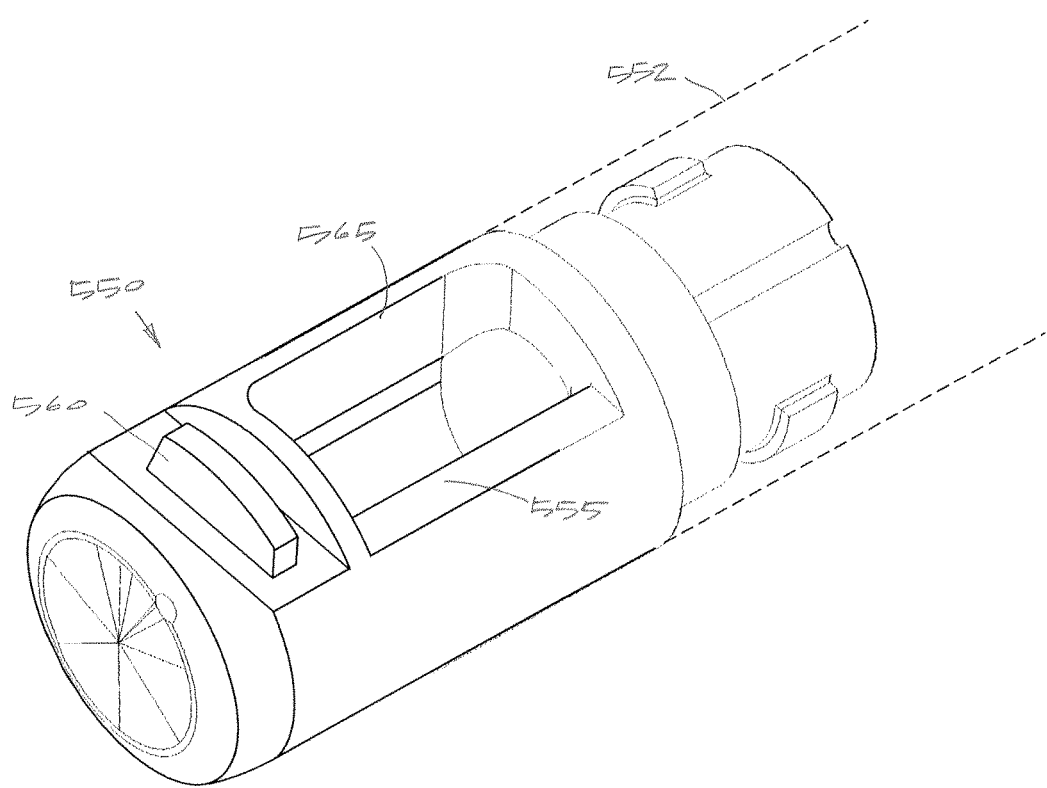
FIG. 16 is a perspective view of a variation of a working end and ceramic member with an electrode adjacent a distal end of an aspiration window having a sharp lateral edge for cutting tissue.

FIG. 16 illustrates another variation of distal ceramic tip 550 of an inner sleeve 552 that is configured without the sharp cutting edges 410 of the embodiment of FIGS. 9-11. In other respects, the arrangement of the window 555 and the electrode 560 is the same as described previously. Further, the outer periphery of the electrode is similar to the outward surface of the ceramic tip 550. In the variation of FIG. 16, the window 555 has at least one sharp edge 565 for cutting soft tissue when the assembly is rotated at a suitable speed from 500 to 5,000 rpm. When the ceramic tip member 550 is maintained in a stationary position and translated over targeted tissue, the electrode 560 can be used to ablate surface layers of tissue as described above.

Figure 17:
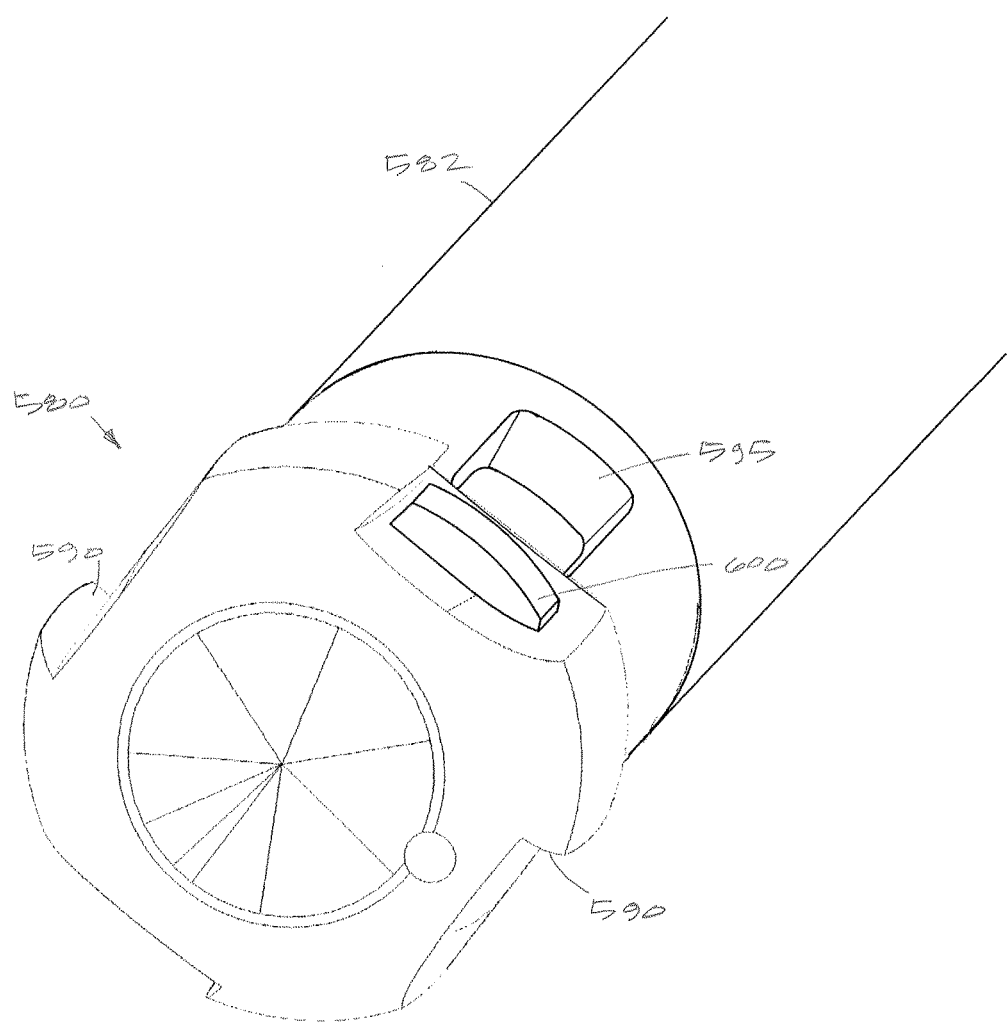
FIG. 17 is a perspective view of a variation of a working end and ceramic member with four cutting edges and an electrode adjacent a distal end of an aspiration window.

FIG. 17 depicts another variation of distal ceramic tip 580 coupled to an inner sleeve 582 that again has sharp burr edges or cutting edges 590 as in the embodiment of FIGS. 9-11. In this variation, the ceramic monolith has only 4 sharp edges 590 which has been found to work well for cutting bone at high RPMs, for example from 8,000 RPM to 20,000 RPM. In this variation, the arrangement of window 595 and electrode 600 is the same as described previously. Again, the outer periphery of electrode 595 is similar to the outward surface of the cutting edges 590.

A number of embodiments of the invention have been described. Nevertheless, it will be understood that various modifications may be made without departing from the spirit and scope of the invention.

What is claimed is:

1. A medical device for removing tissue comprising:
    an elongated sleeve having a longitudinal axis, a proximal end and a distal end;
    a ceramic cutting member with a plurality of ceramic cutting edges defining a cylindrical periphery aligned on the longitudinal axis, the ceramic cutting member extending distally from the distal end of the elongated sleeve;
    an electrode carried by the ceramic cutting member on a surface between the plurality of ceramic cutting edges; and
    a motor drive configured to couple to the proximal end of the elongated sleeve to rotate the ceramic cutting member.

2. The medical device of claim 1 wherein the cylindrical periphery of the plurality of ceramic cutting edges has a radius relative to the longitudinal axis which is at least as great as a radius of a periphery of the surface carrying the electrode relative to the longitudinal axis.

3. The medical device of claim 1 wherein the ceramic cutting member comprises a wear-resistant ceramic material.

4. The medical device of claim 3 wherein the ceramic cutting member consists exclusively of the wear-resistant ceramic material.

5. The medical device of claim 3 wherein the wear-resistant ceramic material is selected from the group consisting of yttria-stabilized zirconia, magnesia-stabilized zirconia, ceria-stabilized zirconia, zirconia toughened alumina and silicon nitride.

6. The medical device of claim 1 wherein the ceramic cutting member has at least one window in a side thereof which communicates with an interior channel of the elongated sleeve which is configured to be connected to a negative pressure source.

7. The medical device of claim 6 wherein the window is adjacent the electrode.

8. The medical device of claim 6 wherein the window is proximal to the electrode.

9. The medical device of claim 6 wherein the window is proximal to the plurality of ceramic cutting edges.

10. The medical device of claim 6 wherein the window is at least partly intermediate the plurality of ceramic cutting edges.

11. The medical device of claim 8 further comprising radio frequency (RF) source connected to the electrode and a controller operatively connected to the motor drive, the RF source and the negative pressure source.

12. The medical device of claim 1 wherein the plurality of ceramic cutting edges comprises 1-100 cutting edges, the ceramic cutting member has a diameter ranging between 2 mm and 10 mm, and the plurality of ceramic cutting edges extend over an axial length ranging between 1 mm and 10 mm.

13. The medical device of claim 1 wherein the plurality of ceramic cutting edges are arranged in a pattern selected from at least one of helical, angled and straight relative to said longitudinal axis.

14. A medical device for removing tissue comprising:
    an elongated shaft having a longitudinal axis;
    a distal tip comprising a cylindrical ceramic member coaxially coupled to a distal end of the elongated shaft;
    a plurality of ceramic cutting edges defining a cylindrical periphery aligned on the longitudinal axis, the cylindrical ceramic member extending distally from the distal end of the elongated shaft;
    a window in a surface of the cylindrical ceramic member connected to an interior channel in the elongated shaft; and
    an electrode in the cylindrical ceramic member positioned spaced-apart from a distal end of the window;
    wherein the interior channel is configured to be coupled to a negative pressure source.

15. The medical device of claim 14 wherein the electrode has a width equal to at least 50% of a width of the window.

16. The medical device of claim 14 wherein at least one side of the window comprises a sharp cutting edge.

17. The medical device of claim 14 wherein the electrode at least partly encircles a distal end of the window.

18. The medical device of claim 14 wherein the ceramic member has a cylindrical periphery and wherein the electrode has an outer surface which lies within the cylindrical periphery.

* * * * *